(12) United States Patent  
Palmerton et al.

(10) Patent No.: US 8,147,577 B2
(45) Date of Patent: Apr. 3, 2012

(54) AIR RECIRCULATION SYSTEM WITH FILTER FLAPS

(75) Inventors: Christopher A Palmerton, Clarence, NY (US); Daniel Palmerton, Amherst, NY (US); Robert O Dean, Tonawanda, NY (US); Jay T Kajdas, Getzville, NY (US); Earnest Mohlau, Amherst, NY (US)

(73) Assignee: Medtek Devices, Inc., Amherst, NY (US)

( * ) Notice: Subject to any disclaimer, the term of this patent is extended or adjusted under 35 U.S.C. 154(b) by 0 days.

(21) Appl. No.: 12/961,245

(22) Filed: Dec. 6, 2010

(65) Prior Publication Data

US 2011/0072771 A1 Mar. 31, 2011

Related U.S. Application Data

(63) Continuation of application No. 12/506,509, filed on Jul. 21, 2009, now Pat. No. 7,892,337, which is a continuation of application No. 10/942,186, filed on Sep. 15, 2004, now Pat. No. 7,597,731.

(60) Provisional application No. 60/503,326, filed on Sep. 15, 2003.

(51) Int. Cl.
*B01D 46/00* (2006.01)

(52) U.S. Cl. ............ 55/385.1; 55/420; 55/482; 55/467; 604/319; 604/322; 604/902

(58) Field of Classification Search ............... 55/385.1, 55/385.2, 385.4, 467, 473, 485; 604/319, 604/322, 902; 454/187
See application file for complete search history.

(56) References Cited

U.S. PATENT DOCUMENTS

| | | | | |
|---|---|---|---|---|
| 4,216,743 A * | 8/1980 | Cohen | ........................ | 119/484 |
| 4,963,134 A * | 10/1990 | Backscheider et al. | ....... | 604/319 |
| 5,645,480 A * | 7/1997 | Spengler | ..................... | 454/187 |
| 6,029,404 A * | 2/2000 | Lewis | ........................... | 52/2.18 |
| 6,203,590 B1 * | 3/2001 | Byrd et al. | ..................... | 55/319 |

* cited by examiner

*Primary Examiner* — Duane Smith
*Assistant Examiner* — Minh-Chau Pham
(74) *Attorney, Agent, or Firm* — Phillips Lytle LLP

(57) ABSTRACT

A filter body having a housing, a cavity for holding a filter media, intake ports each configured to receive an intake tube, and a plurality of intake port flaps configured for movement between a first position which restricts passage of a gas or liquid and a second position which allows passage of a gas of liquid. In one aspect, a filter body has flaps that have a magnet and the housing has an attracting material configured to attract the magnet in at least one of the flaps and configured to hold a flap in the first position. In another aspect, a filter in which a portion of the housing comprises an attracting means is configured to hold a flap in the first position. In another aspect, a filter having a housing configured to hold a filter media has a plurality of fluid passage holes and hole covers, in which the hole covers and an area adjacent to the holes on the filter housing each have an attracting material for holding the hole covers in a position.

14 Claims, 22 Drawing Sheets

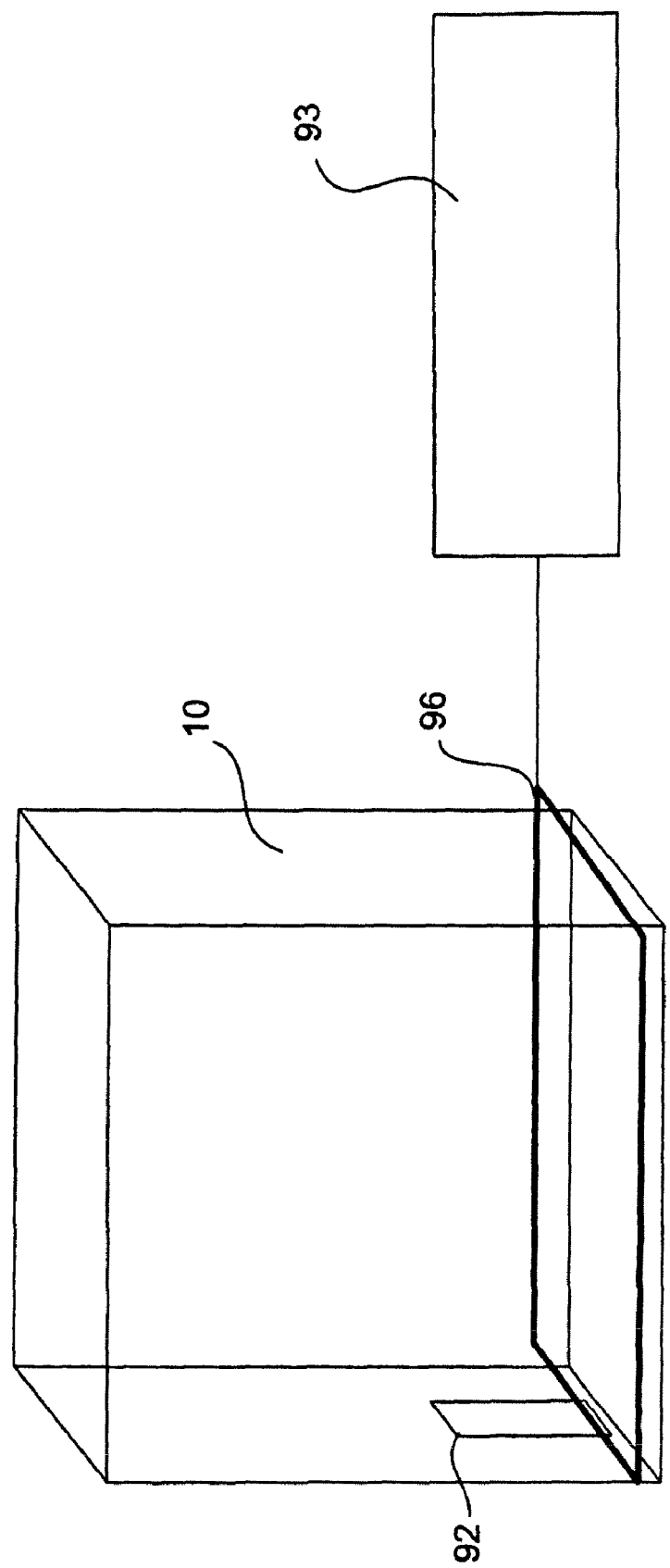

AIR RECIRCULATION SYSTEM WITH FILTER FLAPS

CROSS-REFERENCE TO RELATED PATENT APPLICATIONS

The present application is a continuation of U.S. patent application Ser. No. 12/506,509, filed Jul. 21, 2009, now U.S. Pat. No. 7,892,337 B2, which is a continuation of U.S. patent application Ser. No. 10/942,186, now U.S. Pat. No. 7,597,731 B2, filed Sep. 15, 2004, which claims the benefit of U.S. Provisional Application No. 60/503,326, filed Sep. 15, 2003, each of which is hereby incorporated by reference.

BRIEF DESCRIPTION OF THE DRAWINGS

The nature and mode of operation of embodiments of the air recirculation system will now be described-with reference to the accompanying drawing Figures, in which:

FIG. 5a is a schematic diagram of an RFID circuit used as a filter life timer;

DETAILED DESCRIPTION OF EMBODIMENTS OF THE INVENTION

Initially, it should be appreciated that like drawing numbers on different drawing views identify identical structural elements of embodiments of the air recirculation system with integrated vacuum motor and filter. It also should be appreciated that figure proportions and angles are not always to scale in order to clearly portray the attributes of the described embodiments.

It should be understood that the invention is not limited to the disclosed embodiments. Various modifications and equivalent arrangements are intended to be included within the spirit and scope of the appended claims.

Figure 1:
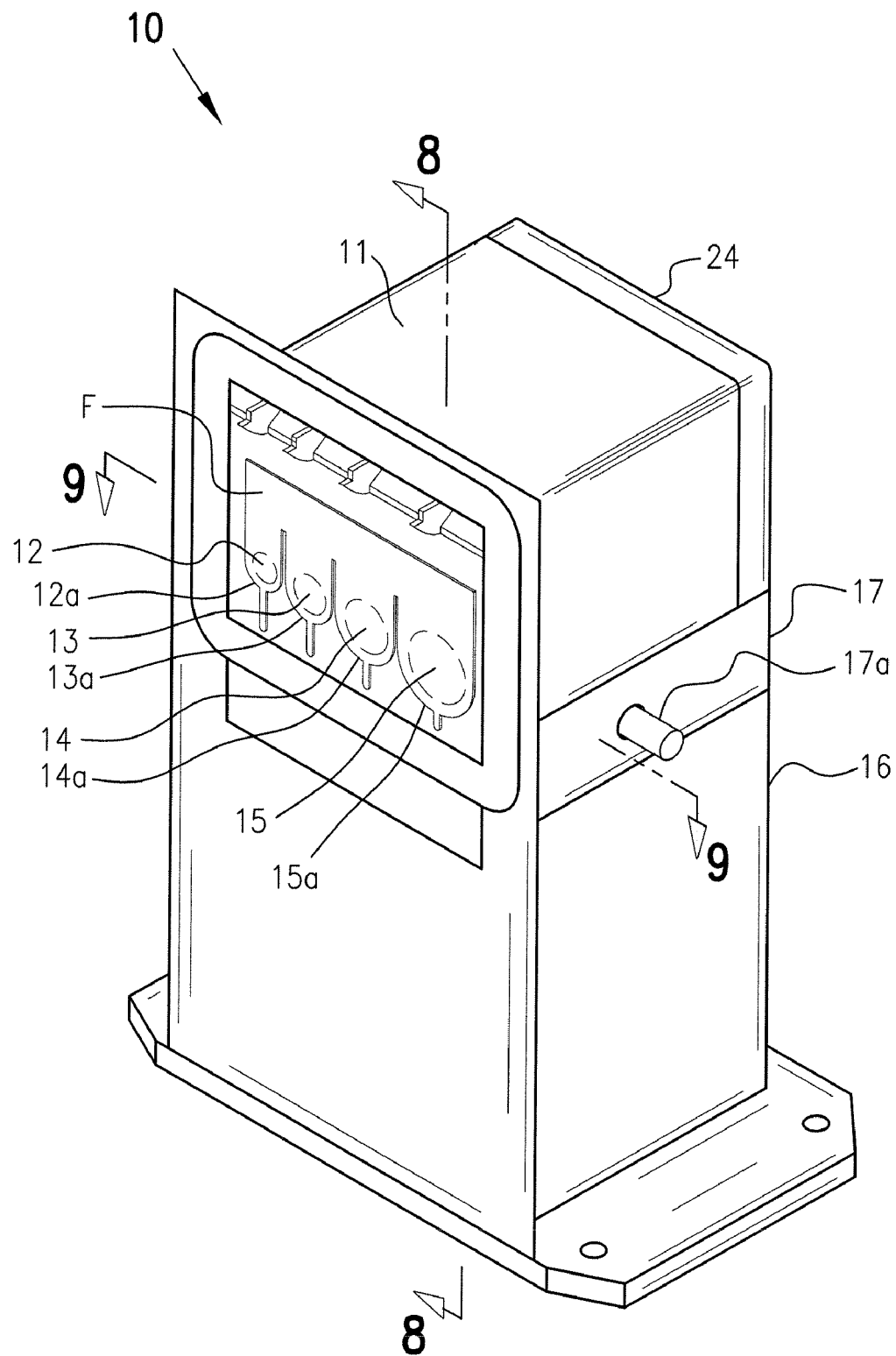
FIG. 1 is a top perspective view of a multi-port filter.

Adverting to the drawings, FIG. 1 is a top perspective view of multi-port filter 10. A housing 11 encloses the filter media (not shown in FIG. 1). In the embodiment shown, intake ports 12, 13, 14, and 15 covered by flaps 12a, 13a, 14a, and 15a, respectively. Intake ports 12, 13, 14, and 15 may be of the same or different sizes and may be fabricated from any releasable adhesive material. In the embodiment shown, flaps 12a, 13a, 14a, and 15a are shown extending from a main flap body F. In an alternative embodiment, each of flaps 12a-15a may be individually attached to housing 11. Flaps 12a-15a may rest on or may be secured over intake ports 12-15, for example, by fabricating flaps 12a-15a from flexible magnetic material and placing magnetic material of opposite polarity on housing 11 or one or more of intake ports 12-15 in such a manner as to attract and hold each flap. Alternatively, magnetic material comprising a hinge or hinge-like crease may be used to cover the intake ports. Further, filter 10 may include metal to attract and releasably hold a magnetic flap.

FIG. 1 also shows multi-port filter 10 in operative connection with a vacuum means, such as a vacuum motor 26, inside a vacuum motor housing 16, via a plenum 24 and a solenoid 17. In an alternative embodiment, the connection between an outlet of multi-port filter 10 and vacuum motor 26 may be fabricated using a tube or hose of sufficient diameter as to permit creation of an adequate air flow from multi-port filter 10 directly to vacuum motor 26 in vacuum motor housing 16.

Figure 2:
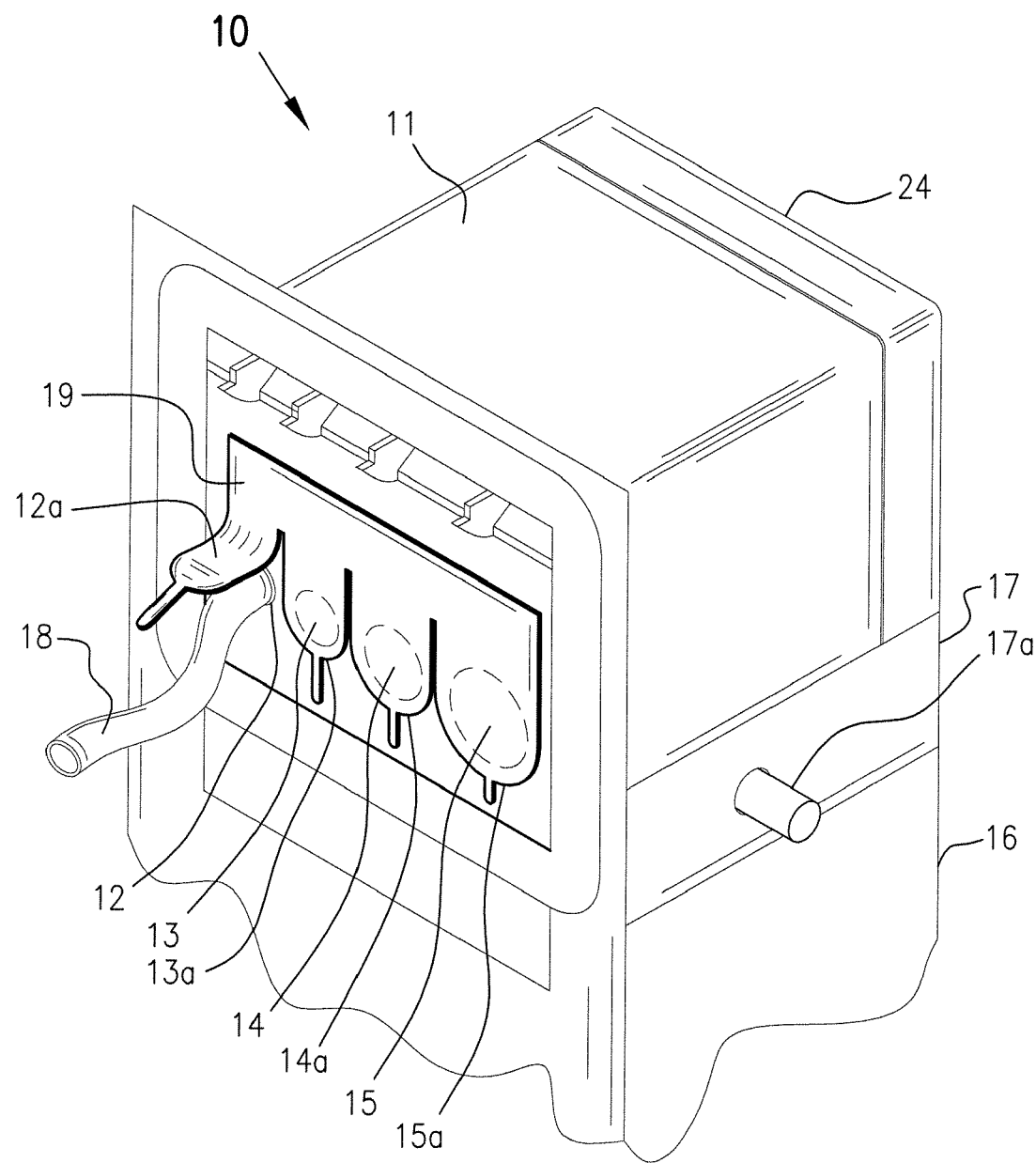
FIG. 2 is a front perspective view of a multi-port filter with intake port covers and a tube connected to an intake port.
Figure 3:
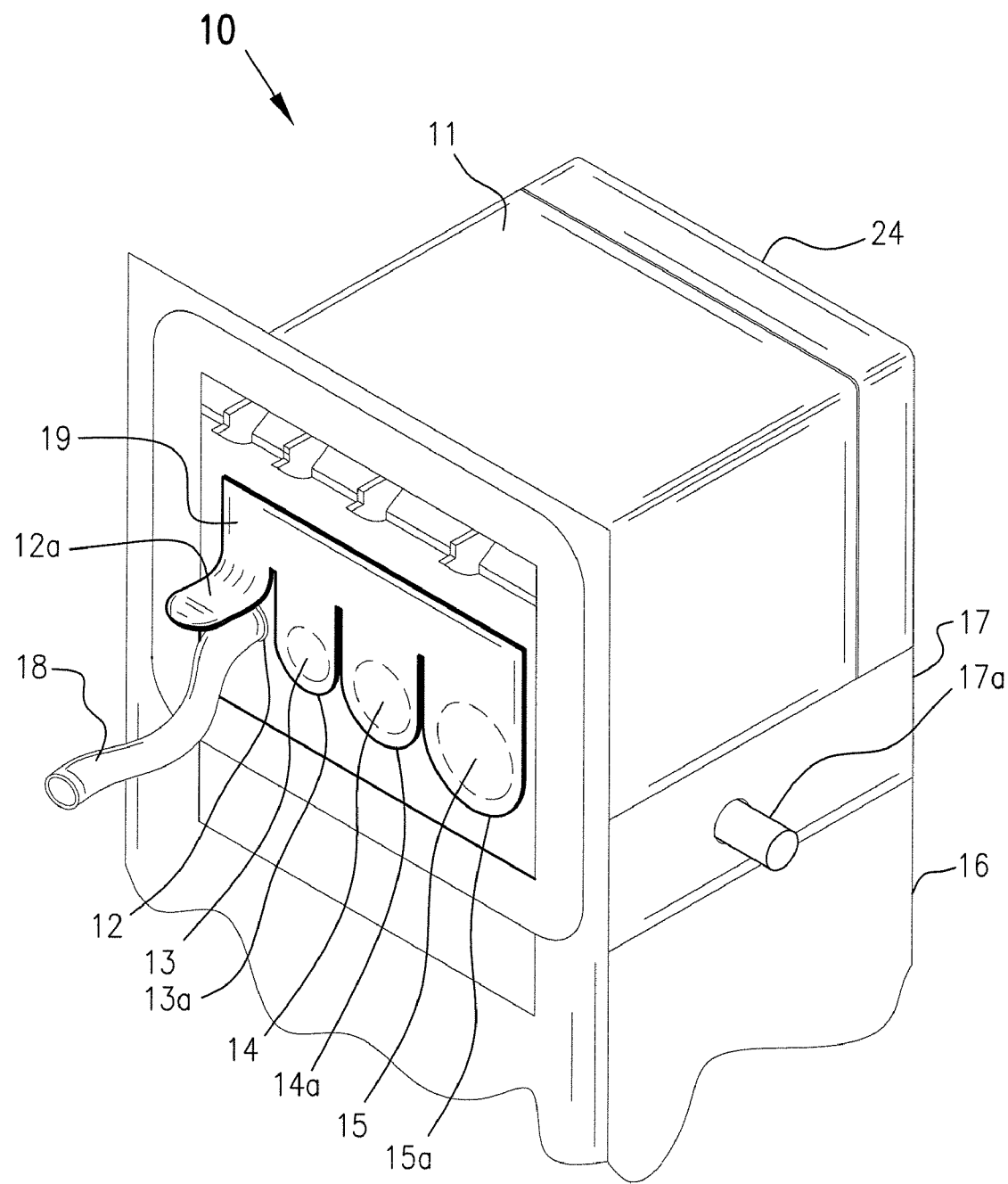
FIG. 3 is a front perspective view of a multi-port filter showing alternative intake port covers.

FIGS. 2 and 3 are front perspective views depicting an intake tube 18 connected to intake port 12. Flaps 13a, 14a, and 15a remain in place covering intake ports 13, 14, and 15, respectively. It will be recognized that the vacuum created by the air flow through tube 18 and intake port 12 is enhanced by maintaining flaps 13a-15a in place over intake ports 13-15, respectively. It can also be understood that more than one intake port may be used at the same time. A solenoid arm 17a is shown extending from solenoid 17. FIGS. 2 and 3 also show plenum 24 in direct connection to filter housing 11. In addition, FIG. 3 depicts an alternative embodiment of flaps 12a-15a.

Figure 4:
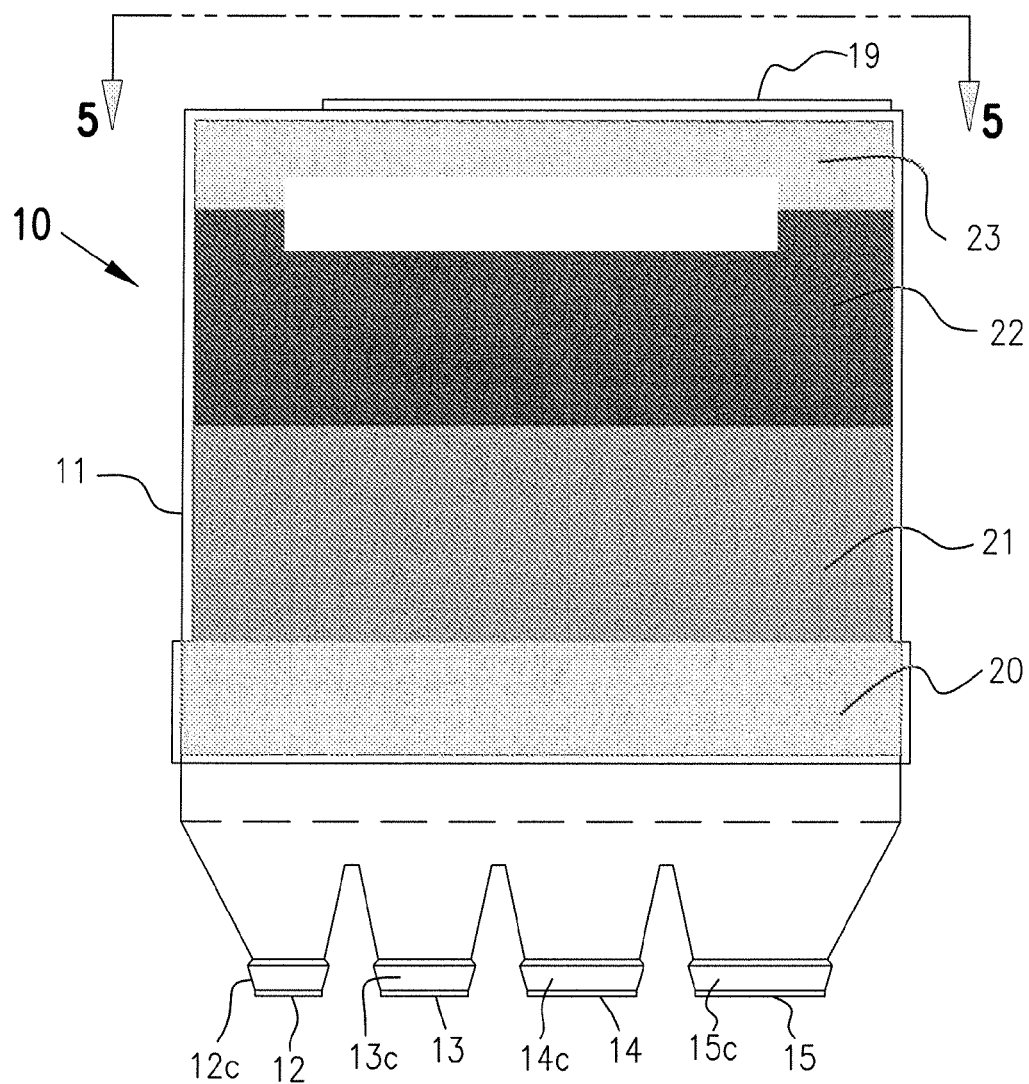
FIG. 4 is a top view of a preferred embodiment of a multi-port filter having layers of filter media.

FIG. 4 is a top view of multi-port filter 10 showing different layers of filter media included within filter housing 11. A gasket 19 surrounds one or more filter outlets 19a (not shown in FIG. 4) allowing for a direct seal between outlets 19a of filter 10 and plenum 24.

A pre-filter layer 20 is configured to entrap and retain particles from smoke or other vapors found in the atmosphere of the area where multi-port filter 10 is in operation. A suitable pre-filter material is a polyester filter media available from Mart Corporation, Sanford, N.C. having a weight of about 4 ounces per square yard and a thickness of approximately 0.5 inch. Pre-filter layer 20 is constructed to entrap and contain particulate on the order of 3.0 microns or greater. Other suitable materials, such as hydrophobic materials, which are well known to those skilled in the art, may also be used. An example of such hydrophobic material is expanded PTFE membrane from W.L. Gore and Associates, Inc. of Elkton, Md.

A second filter layer 21, configured to retain particles 3 microns or less in size, is shown in FIG. 4. Second filter layer 21 may be formed from a UPLA (ultra low penetration air) material that entraps and contains particulate matter having a size of 0.12 microns or greater at an efficiency of 99.999%. A suitable ULPA filter media is High Alpha UPLA No. 6550 or greater provided by Lydall International of Merland, France. Other suitable materials are well known to those skilled in the art. ULPA layer 21 may include an antimicrobial material blended with a polymer material of the ULPA particulate filtration media. A typical antimicrobial material is a clay or other carrier material containing heavy metals such as tin or silver. Second filter layer 21 may be provided with antimicrobial properties by coating the exterior of the strands comprising ULPA layer with an antimicrobial. In an alternative embodiment, antimicrobial properties may be incorporated in ULPA layer 21 by embedding an antimicrobial homogenously throughout each strand of ULPA layer 21. A suitable antimicrobial material is Microban.®. Additive B supplied by Microban Products Company of Huntersville, N.C.

Multi-port filter 10 may also include an activated carbon layer 22 and/or a post filter layer 23. Activated carbon layer 22 is comprised of activated charcoal or other suitable materials well known in the art designed to entrap and contain gases, odors, organic vapors, and toxins that may be present in the atmosphere being filtered. Post-filter layer 23 is formed from any material suitable to entrap and contain particulate matter, such as melt blown polypropylene media with polypropylene facing and backing. An example of suitable post-filter material is Delta Aire.™. Filtration Media from Johns Manville of Denver Colo. having an atmospheric efficiency range of 90-95% at 0.5 microns. Post-filter layer 23 may be placed in series downstream from activated carbon layer 22 to entrap and contain activated carbon fines.

Although multi-port filter 10 is shown with all filter layers contained in a single housing 11, in an alternate embodiment, one or more of the filter layers may be contained in a separate cartridge with inputs and outputs creating a pathway for a fluid stream to pass through separate filter layer cartridges. Such an embodiment allows for the individual changing of separate filter layers at different times rather than all filter layers at the same time.

Although female intake ports 12-15 are shown in FIGS. 1-3, it is possible to use as an alternative embodiment intake ports 12-15 in which each intake port is in the form of a male projection as shown in FIG. 4. The connection between a tube or hose and each of intake ports 12-15 is sealed by placing an end of the tube or hose over tapered ends 12c-15c which surround the perimeter of intake ports 12-15, respectively. Alternatively, a bead may be used to create a suitable seal.

Figure 5:
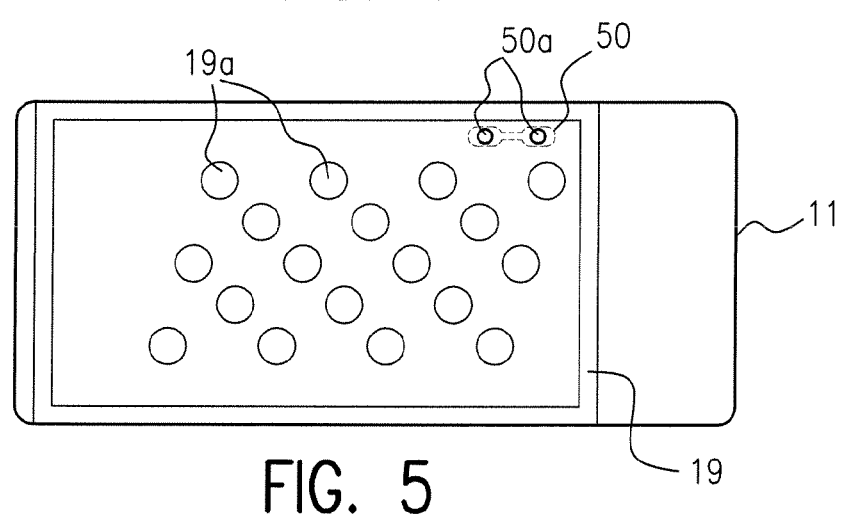
FIG. 5 is a partial rear view of a multi-port filter with a plurality of filter outlets and one embodiment of a filter life timing device surrounded by a rear gasket.

FIG. 5 is a rear view of multi-port filter 10 showing plurality of outlets 19a surrounded by gasket 19. Use of gasket 19 allows for a direct connection of multi-port filter 10 to plenum 24 without an intervening duct, tube, hose, or similar structure. Gasket 19 may be of any size provided all outlets 19a are enclosed within the perimeter of gasket 19 and an airtight seal is formed with plenum 24. Plenum 24 directs the airflow from multi-port filter 10 to vacuum motor 26. Such a configuration allows for use of multi-port filter 10 and vacuum motor 26 in a relatively small space.

Figure 6:
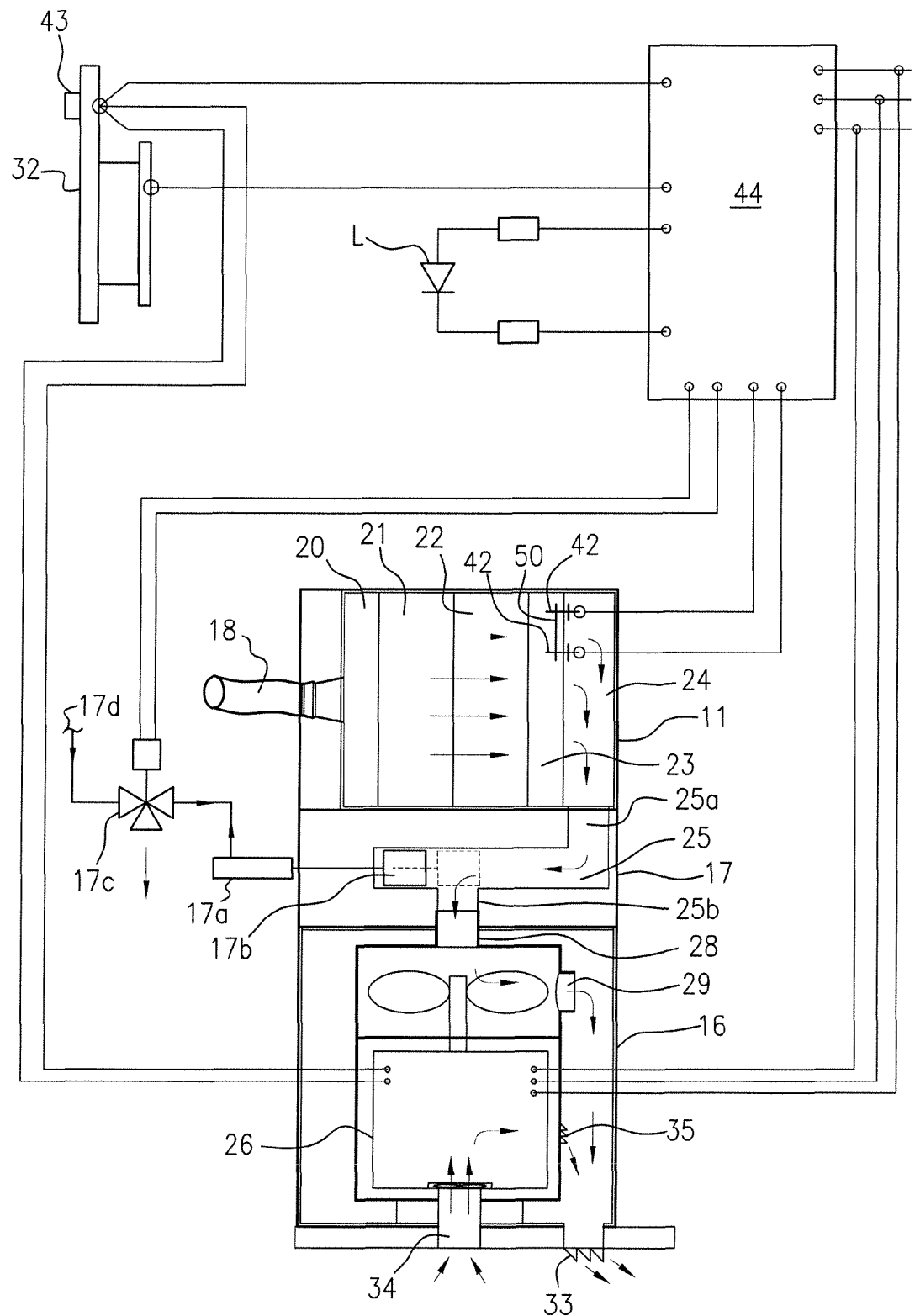
FIG. 6 is schematic diagram of a timer reset circuit.

To limit the use of a filter to its designed life, it is helpful to provide one or more mechanisms and/or methods designed to inactivate the system in which the filter is being used after the desired filter life is reached. FIG. 5 reveals an embodiment in which multi-port filter 10 incorporates timer rest tab 50. Timer reset tab 50 includes a strip fabricated from copper or other conductive material that is attached to an inside wall of filter housing 11 positioned so as to be exposed through an aperture 50a. FIG. 6 is a schematic diagram of one embodiment of control circuitry utilized to measure the depletion of filter life of multi-port filter 10. The function of timer reset tab 50 and the control circuitry shown in FIG. 6 will be discussed below.

Figure 7:
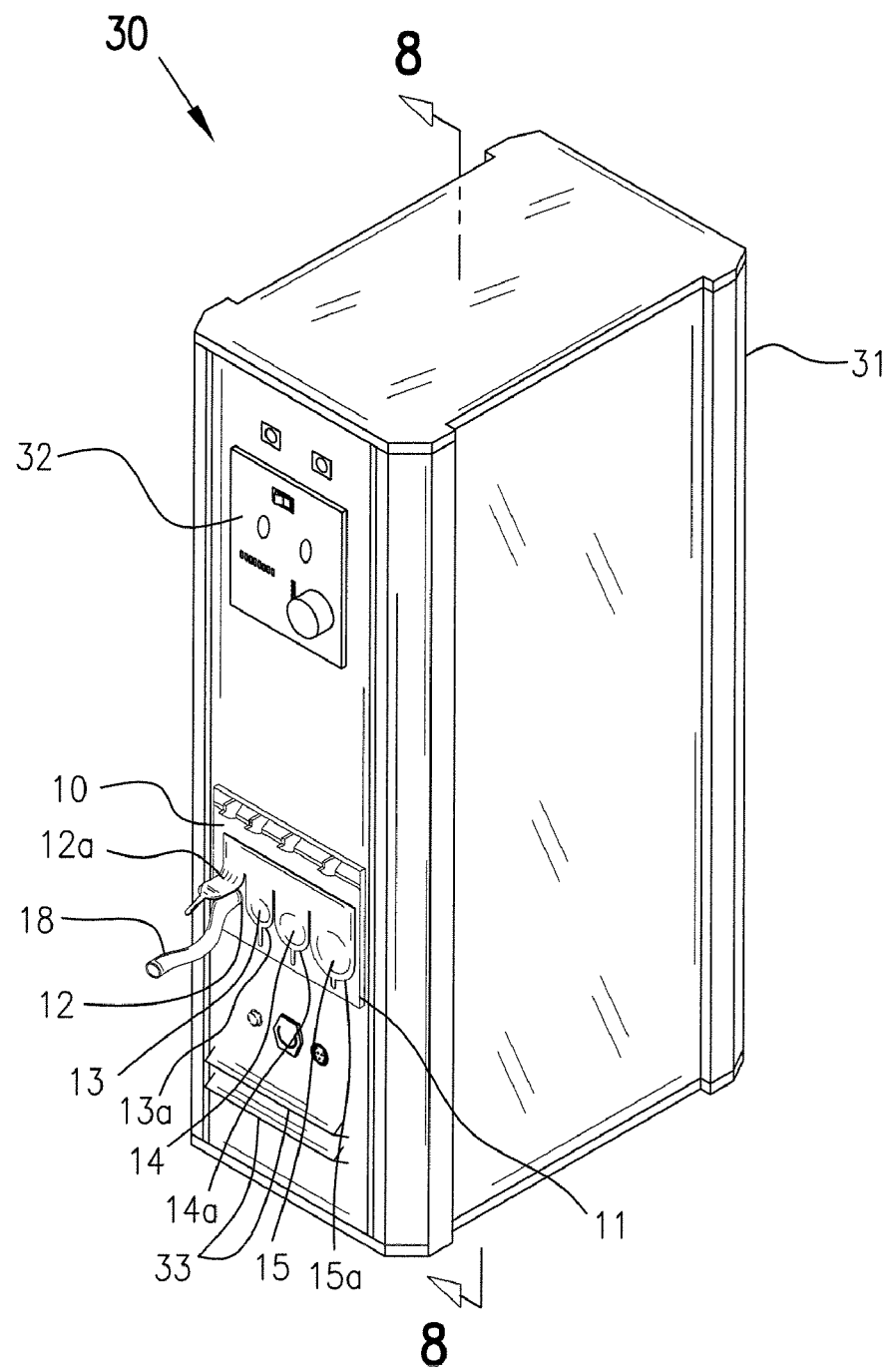
FIG. 7 is a front perspective view of a service head recirculation system.

FIG. 7 is a front perspective view of an embodiment of recirculation system 30. Service head housing 31 encloses recirculation system 30, which includes control panel 32 and exhaust vents 33. Filter 10 is shown with hose 18 fitted into intake port 12.

Figure 8:
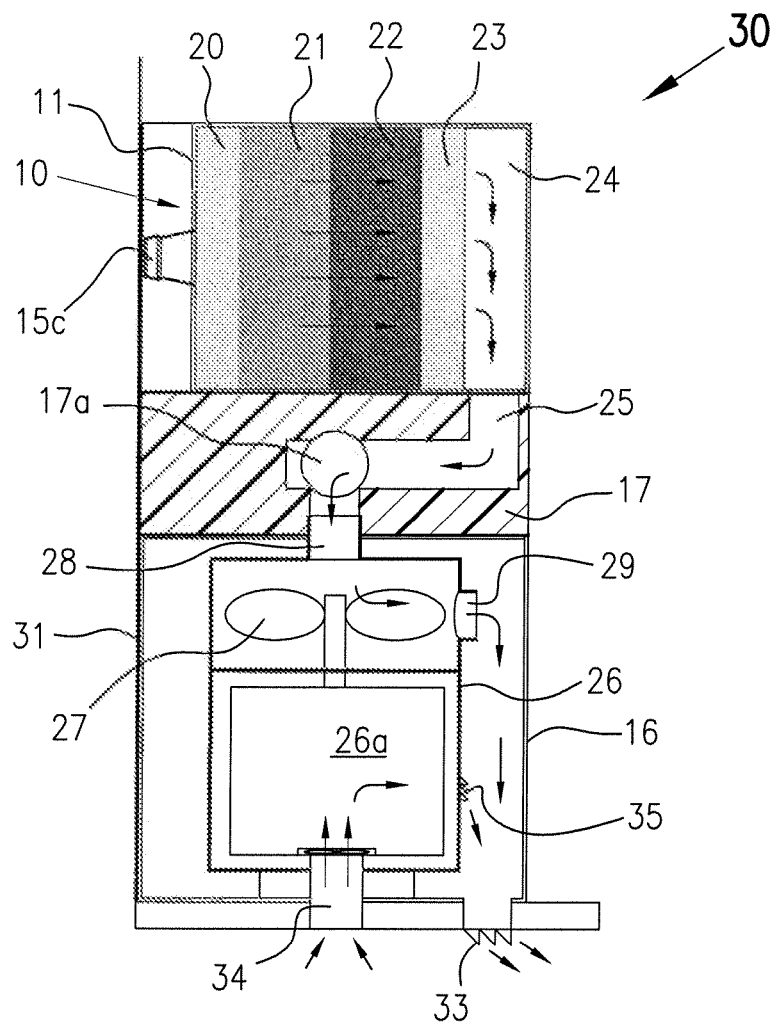
FIG. 8 is a cross-sectional view taken along lines 8-8 of the service head recirculation system of FIG. 7.

FIG. 8 is a cross-sectional view of recirculation system 30 contained within housing 31 taken along lines 8-8 of FIG. 7. Arrows are used to depict the airflow from intake 15 of multi-port filter 10 to exhaust vents 33. A service head may be defined as a housing suspended above the floor of an enclosure, as shown, for example in FIG. 21. The service head receives compressed air, gas and electrical conductors from within or outside the enclosure and provides outputs for the supply of electrical, compressed air and gas to surgical assemblies and/or the operative site. Examples of an enclosure include, but are not limited to, an operating room, a doctor's office, medical ambulatory center, emergency room and similar locations. It will be recognized that enclosures are not limited to medical facilities. Air enters intake port 15 and, in the embodiment shown, travels through pre-filter layer 20, second filter layer 21, activated carbon layer 22 and post-filter layer 23 through outlets 19a (not shown) to plenum 24. Plenum 24 directs the air, shown by the arrows, toward solenoid block 17. When full power is applied to vacuum means 26, in this case a vacuum motor, solenoid arm 17a is actuated to move solenoid plug 17b (FIG. 9) from channel 25, thereby allowing full air flow through channel 25 through motor intake 28 to vacuum means 26. Impeller 27 moves the filtered air through motor outlet 29 into vacuum means housing 16 and out exhaust vents 33. In addition, air is drawn through cooling intake 34, over the motor windings 26a, and out cooling vent 35. The cooling air following this path, used to cool motor 26, mixes with the filtered air and is exhausted through exhaust vents 33. In one embodiment, exhaust vents 33 direct the exhausted air away from cooling intake 34 to prevent the recirculation of the same cooling air over motor windings 26a.

Figure 9:
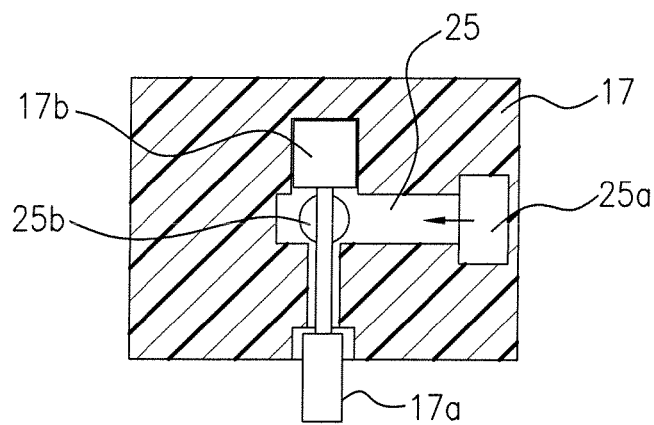
FIG. 9 is a plane view of a solenoid block taken along line 9-9 of FIG. 1.

FIG. 9 is a plane view of solenoid block 17 taken along line 9-9 of FIG. 1 demonstrating how the solenoid system is used to control airflow. Filtered air from plenum 24 is received in solenoid block 17 through intake portion 25a of channel 25. Vacuum motor 26 (not shown in FIG. 9) pulls filtered air along channel 25 to exit port 25b leading to motor intake 28. As shown in FIGS. 8 and 9, the path of the filtered air from plenum 24 includes two right angle turns leading to motor intake 28. This arrangement of plenum 24, solenoid block 17, and channel 25 is well suited for the arrangement of components depicted in the various figures, however other configurations may be utilized for other component layouts.

Figure 10:
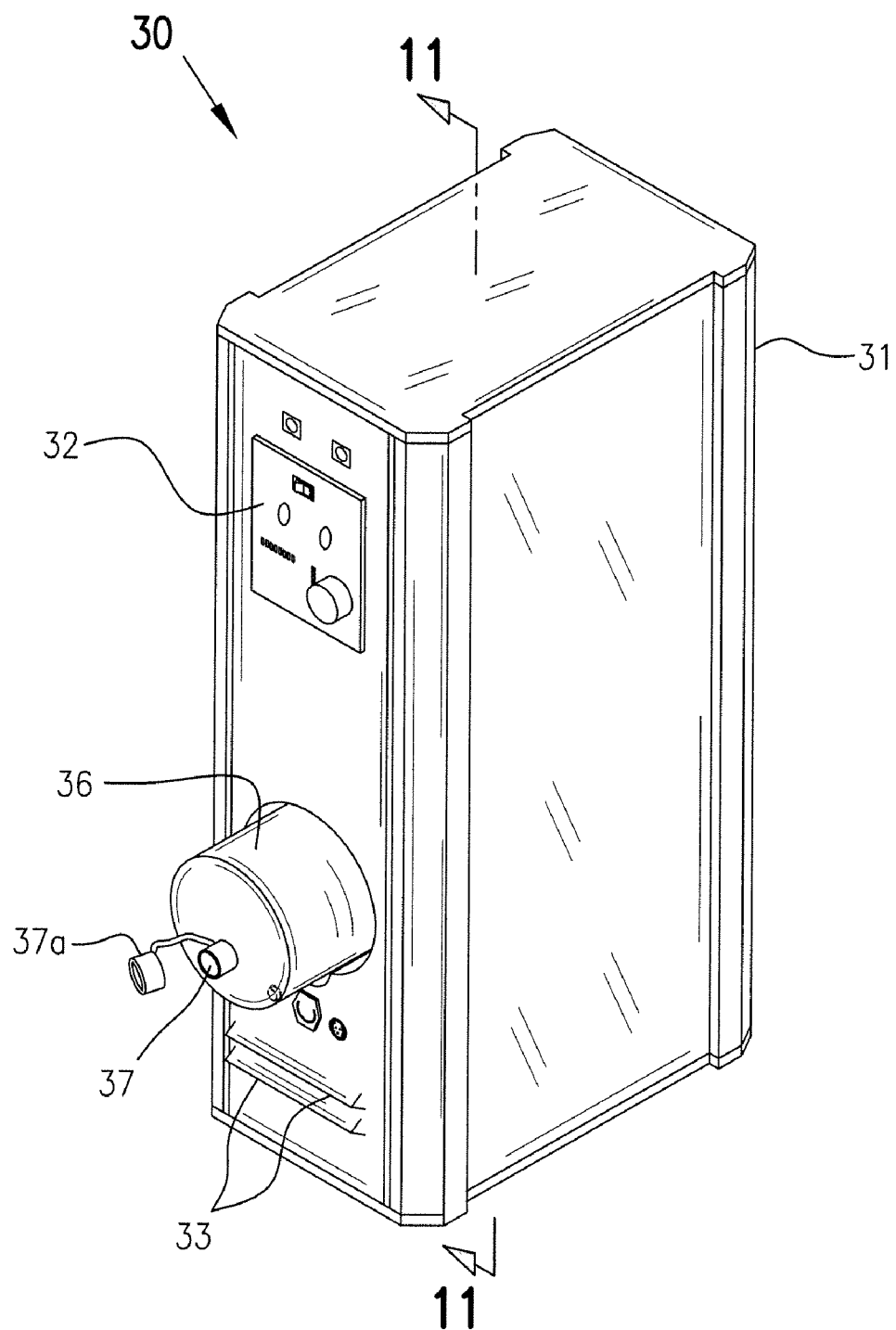
FIG. 10 is a front perspective view of an alternate embodiment of a service head recirculation system.

FIG. 10 is a top perspective view of an alternate embodiment of recirculation system 30 in which a single intake port filter 36 is utilized to filter the intake air. Intake 37 receives a hose or tube into which contaminated intake air is pulled by vacuum motor 26 (not shown in FIG. 10) through filter 36. Filter 36 may include an intake cover 37a.

Figure 11:
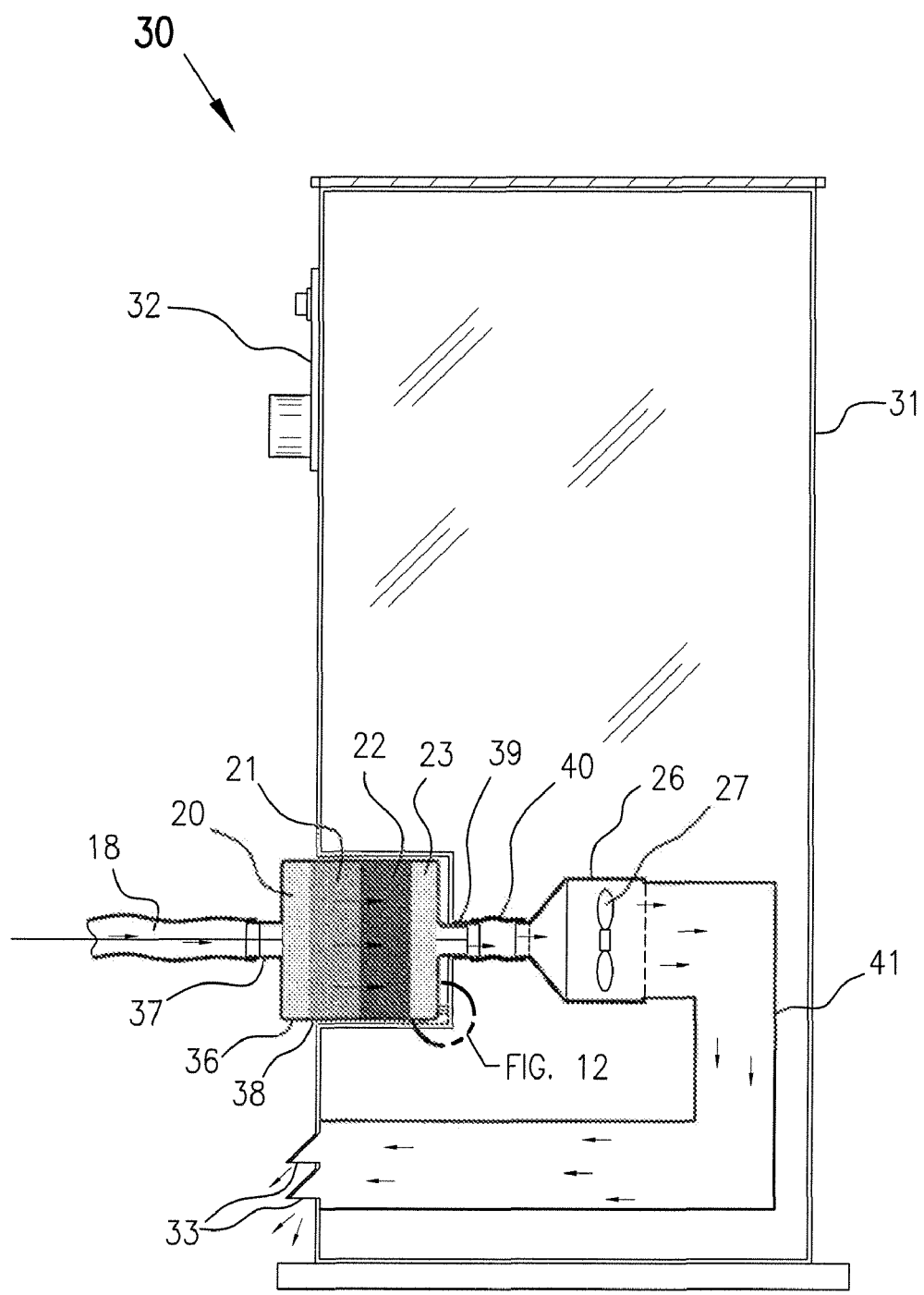
FIG. 11 is a cross-sectional view of the service head recirculation system taken along line 11-11 of FIG. 10.

FIG. 11 is a schematic cross-sectional view taken along line 11-11 in FIG. 10. Filter 36 is seen seated in socket 38, which is herein defined as a space that is designed to receive a filter. Intake hose 18 is attached to intake 37. In the embodiment shown, contaminated air is pulled by vacuum motor 26 from a contamination source into intake hose 18 through pre-filter layer 20, second filter layer 21, activated carbon layer 22 and post-filter layer 23. A connection hose 40 connects filter outlet 39 to vacuum motor 26. Vacuum motor 26 turns impeller 27 to force air along duct 41 to exhaust vents 33, where filtered air is vented to the room. Persons skilled in the art will recognize that connection hose 40 may be fabricated from either flexible or rigid materials as long as a satisfactory seal is maintained.

Figure 12:
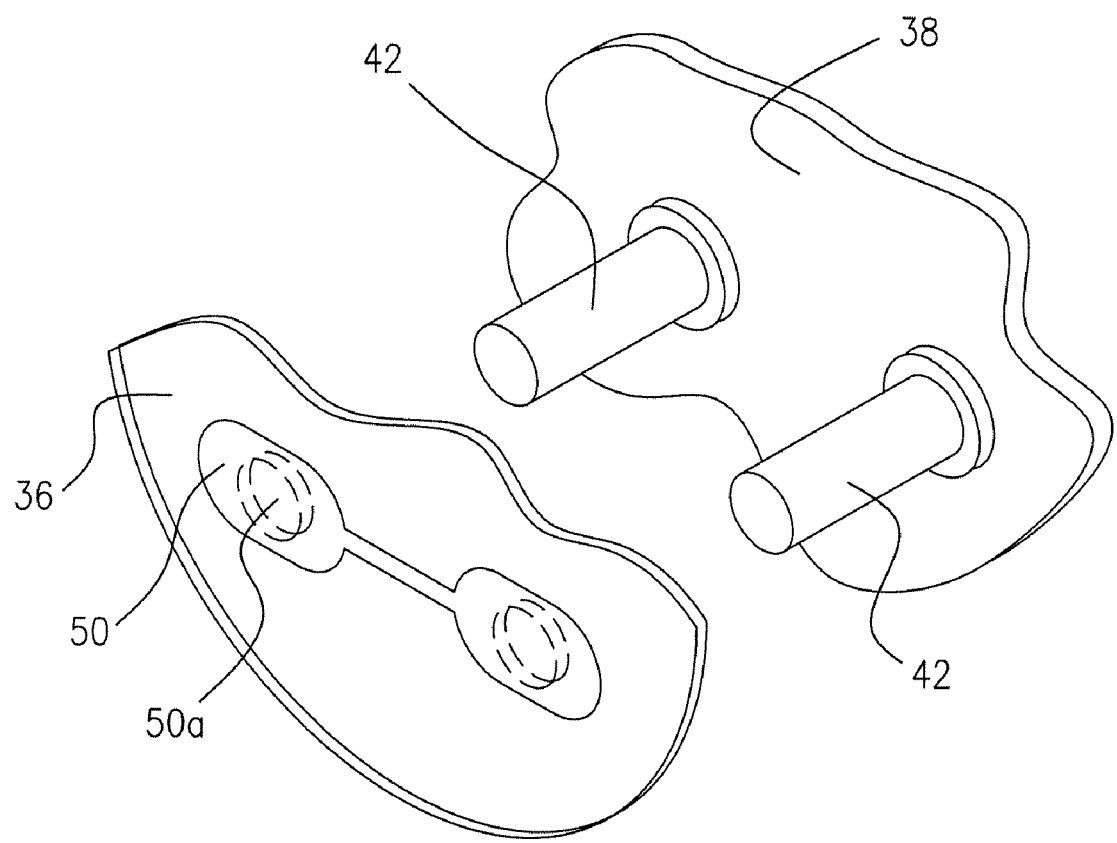
FIG. 12 is a magnified view of the circled components in FIG. 11.
Figure 13:
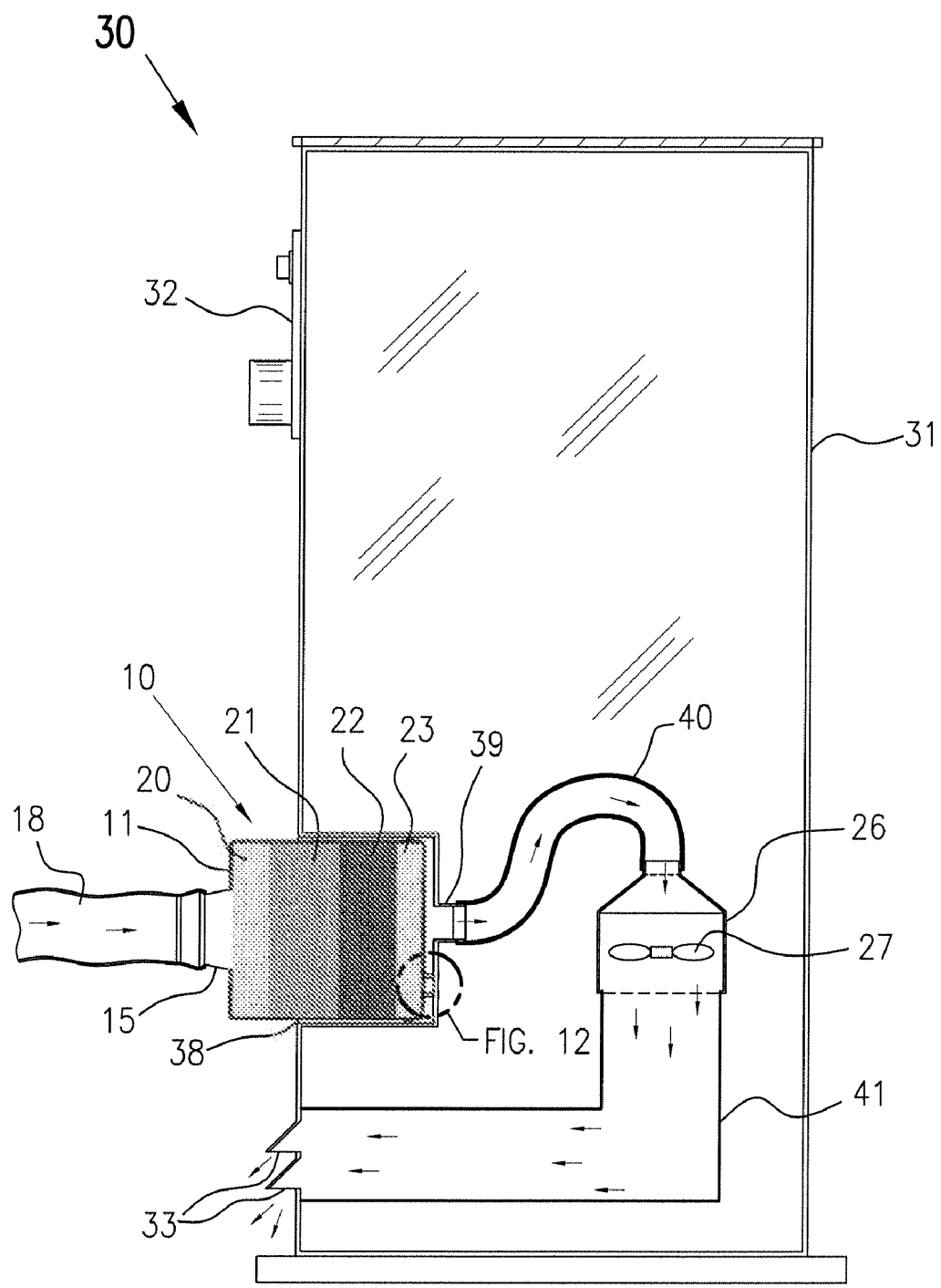
FIG. 13 is a cross-sectional view of a service head recirculation system with a multi-port filter.

FIG. 12 is a magnified view of the circled components in FIG. 11. As shown in FIG. 12, a rear wall of filter socket 38 incorporates timer reset pins 42. When filter 36 is placed into filter socket 38, timer reset tab 50 is punctured by timer-reset pins 42. During the period when timer reset tab 50 and timer reset pins 42 are in contact before timer reset tab 50 is broken, a timer located in recirculation system 30, preferably in control panel 32, is reset to a predetermined filter life. As long as power is sent to vacuum motor 26, the timer will count down the filter life. If power to vacuum motor 26 is turned off, the timer stops and saves the instant filter life countdown in memory. When power is resupplied to vacuum motor 26, the timer resumes the count down process. When the timer records zero time remaining, the power is turned off. Control panel 32 signals zero filter life has been reached with a display such as a flashing light, zero digital reading, audible warning sign or other suitable device well known in the art. In one embodiment, power to vacuum motor 16 remains on after zero time is reached. However, if the main power is turned off it cannot be restarted until a new filter is placed into filter socket 38.

In an alternative embodiment, power is supplied to recirculation system 30 and activates control panel 32, timer displays and other components. Vacuum motor 26 is activated by turning on a separate motor off/on control switch. In this embodiment, after filter life reaches zero, vacuum motor 26 cannot be turned on by the off/on switch after it has been off for a predetermined amount of time unless a new filter is placed into filter socket 36, even if the main power is continuously applied to control panel 32.

FIG. 6 depicts schematically a diagram of a typical timing circuit. Solenoid plug 17b is attached to solenoid arm 17a. In one embodiment, power supplied to motor 26 can be adjusted using mode control switch 43 to control the count rate of the timer depending on the location of the contaminant source. For example, modes can designate open or high flow, laparoscopic flow, and/or surgical pen flow, each causing the timer to count down filter life at a different rate. Control signals are sent to solenoid valve 17c to move solenoid arm 17a to an unblocking position, as shown in FIG. 9, for high air flow, or to move it to a position to partially block channel 25 to reduce the flow of filtered air to vacuum motor 26. Simultaneously, signals are sent to the timer on control panel 32 to adjust the count down rate of remaining filter life. As airflow through multi-port filter 10 or filter 36 is increased, the rate of count down of remaining filter life is also increased. Conversely, as airflow through multi-port filter 10 or filter 36 is reduced, filter life is counted down at a slower rate. A separate motor control switch controls the speed of vacuum motor 26. In one embodiment, the speed of vacuum motor 26 may be controlled by regulating the amount of voltage applied to vacuum motor 26. Other methods and devices for controlling motor speed may also be used. These include devices such as mass flow sensors to measure flow rate of intake air and subsequent programmed correlation with rate of filter life reduction and motor speed sensors to correlate filter life reduction with the speed of vacuum motor 26. Circuits on high voltage panel 44 are configured to reduce line power received from a power source to voltages suitable for use in recirculation system 30. Indicator light L is configured to indicate power to recirculation system 30 is on. It will be obvious to those skilled in the art that several embodiments of this system may be employed. For example, solenoid block 17 may be in a normally open or normally closed position. Further, the speed of vacuum motor 26 may be regulated independently of the filter life countdown rate utilized by the operator. Additionally, filter life may be displayed as a measure of remaining filter life or accumulated filter usage. Also, filter life may be measured by changes in pressure drop between the input and output sides of multi-port filter 10 or filter 36.

In an alternate embodiment, multi-port filter 10 may include one or more of a variety of integrated circuits to monitor remaining or accumulated filter life. Examples of such integrated circuits include an RFID tag with an antenna fixed on or within multi-port filter 10 in communication with and RFID antenna and electronics in recirculation system 30 wherein such communication would include the transmission of changing filter operating life information between multi-port filter 10 and recirculation system 30. The RFID tag includes a memory portion, which stores the filter profile. A filter profile includes information regarding filter history including, but not limited to, type of filter, manufacturing batch number and/or serial number, rated filter life, date of manufacture, and a free form notepad. In addition, the RFID tag possesses a transmission portion enabling it to communicate filter profile information to a microcontroller or other controlling device in contaminant removal system 30. Through this communicated information, the microcontroller is able to monitor the depletion of filter life for each individual filter. In one embodiment, an RFID tag reader supports the ISO15693 standard for communicating with tags at 13.56 MHz. One example of an RFID tag reader is a TI 56700 RFID reader manufactured by Texas Instruments.

It is important that the antenna in the RFID system generate a voltage within the tag circuit to enable the tag to operate. An inductive antenna may be used formed from one or more loops of wire with each additional loop approximately doubling the inductance of the antenna. To maximize the efficiency of the antenna, a parallel resonate circuit may be used and tuned to the ISO 15693 frequency of 13.56 MHz. In one embodiment, the planes of the loop antenna and the tag are parallel. However, if conductive material is between the antenna and the tag or within an inch of the tag or antenna, the operational range of the RFID system is affected. In one embodiment, an antennal loop can be oriented around filter housing 38 and positioned such that the tag is within approximately 0.5 inches from at least part of the antenna. In another embodiment, as shown in FIG. 5a, an edge of tag 92, shown as a rectangular tag, is aligned in a parallel plane with the antenna associated with filter 10 and filter housing 11. Antenna 91 is connected to microcontroller 93 and has a bidirectional clock controlled by the microcontroller during command/data write operations. It will be recognized that the RFID filter system can be used with other systems for evacuating particulate matter, including control service head 50 described below. It will be recognized by those skilled in the art that the RFID system described above or the other timing device described herein may be utilized for any similar type of filter. For example, a single intake filter, such as VIROSAFE FILTERS, manufactured by Buffalo Filter of Amherst, N.Y. used for filtering a contaminant from a fluid stream can utilize the RFID circuit to measure filter life. Moreover, such RFID circuits are not confined to filters used to filter smoke and other particulates originating from a surgical site. Such filters having RFID systems may be used on smoke evacuators. An example of such evacuators is the PLUMESAFE Smoke Evacuators manufactured by Buffalo Filter of Amherst, N.Y. or equivalent devices.

Alternate embodiments of integrated circuits include an EPROM or a microcontroller. An EPROM is programmed for a specific number of filter life hours. As a filter is used, the EPROM records the reduction in filter life. After zero filter life is reached, vacuum means 26 is shut off, a new filter is installed and the EPROM is reset to the programmed filter life. In one embodiment, the EPROM will not shut down vacuum means 26 at zero filter life, but will not allow a restart after power to vacuum means 26 is shut off until the filter is replaced. It will be recognized that filters other than multi-port filter 10 or filter 36 may include such integrated circuits.

Other embodiments of filter life timers (not shown) include, but are not limited to, such devices as pressure drop indicators and traps with on-off floats. Pressure drop indicators are used to indicate filter usage by increasing flow pressure differential between the input and output side of the filter. Traps with on-off floats include a part that gradually floats upward to shut off a filter as contaminants accumulate in the trap.

In addition, a remote controller, such as an RS232 interface may be used to control either recirculation system 30 or a surgical assembly control service head 50, as described below. The remote controller may be connected to a microcontroller, computer, or other device that controls recirculation system 30 or control service head 50.

Figure 14:
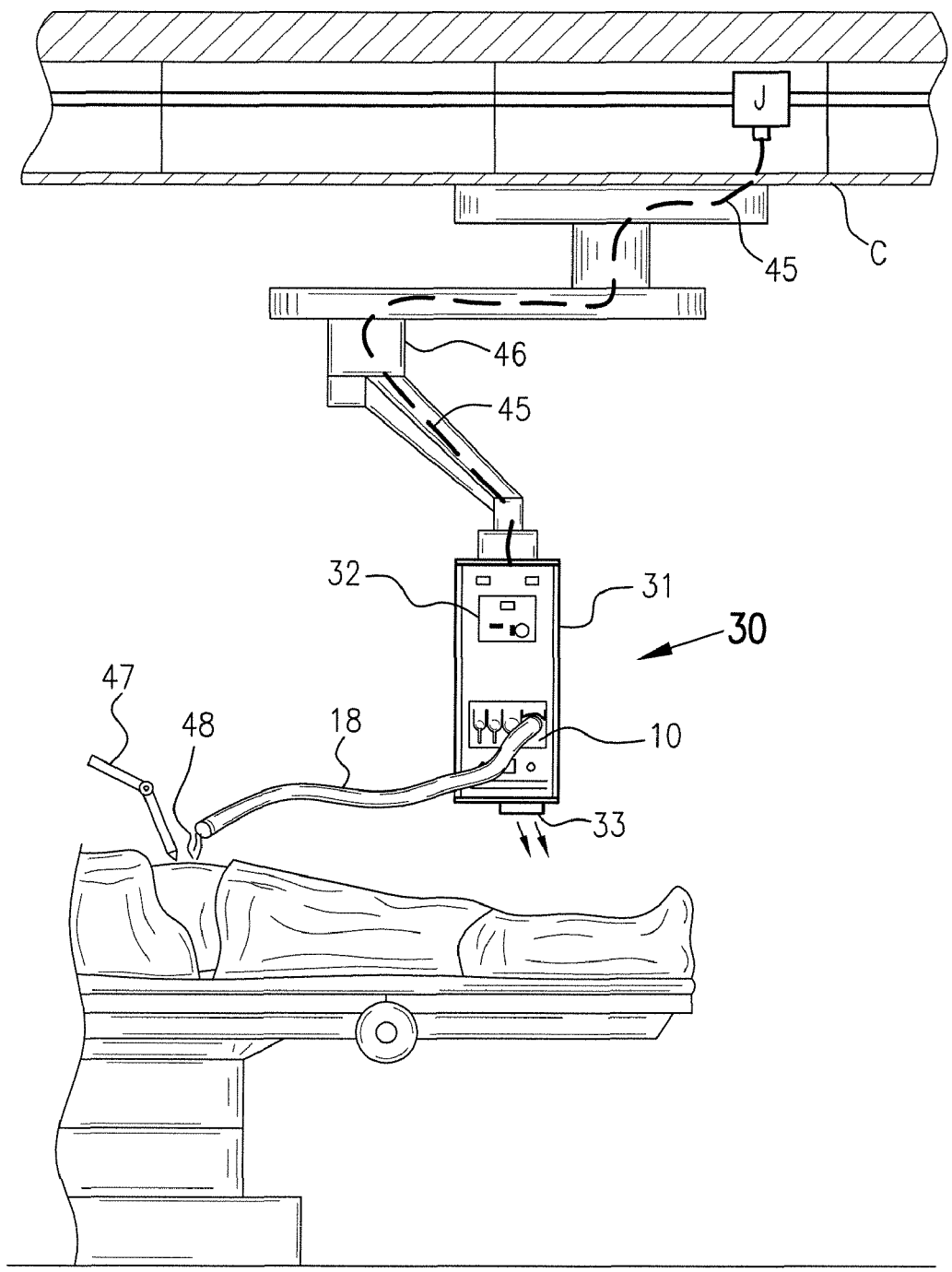
FIG. 14 is a front view of a service head recirculation system with a multi-port filter in an operating room.

FIG. 14 demonstrates the use of multi-port filter 10 and recirculation system 30 in a typical enclosure, such as a hospital operating room. Housing 31, containing multi-port filter 10 incorporated into recirculation system 30, is attached at one end to an articulating arm 46. In the embodiment shown, articulating arm 46 enables the positioning of recirculation system 30 into a position most suitable for the user. Power line 45 extends from junction box J, above ceiling C, to high voltage panel 44. Intake hose 18 extends from a contaminant source 48 to an intake port 12-14 on multi-port filter 10. In the embodiment shown, exhaust vents 33 are located at a bottom of housing 31 and direct filtered air into the enclosure. Surgical instrument 47 may be a laser, an electrosurgical pen, or other device that generates smoke, contaminants, or particles during surgery. As discussed above, other filters, such as filter 36, may be utilized with recirculation system 30.

Figure 15:
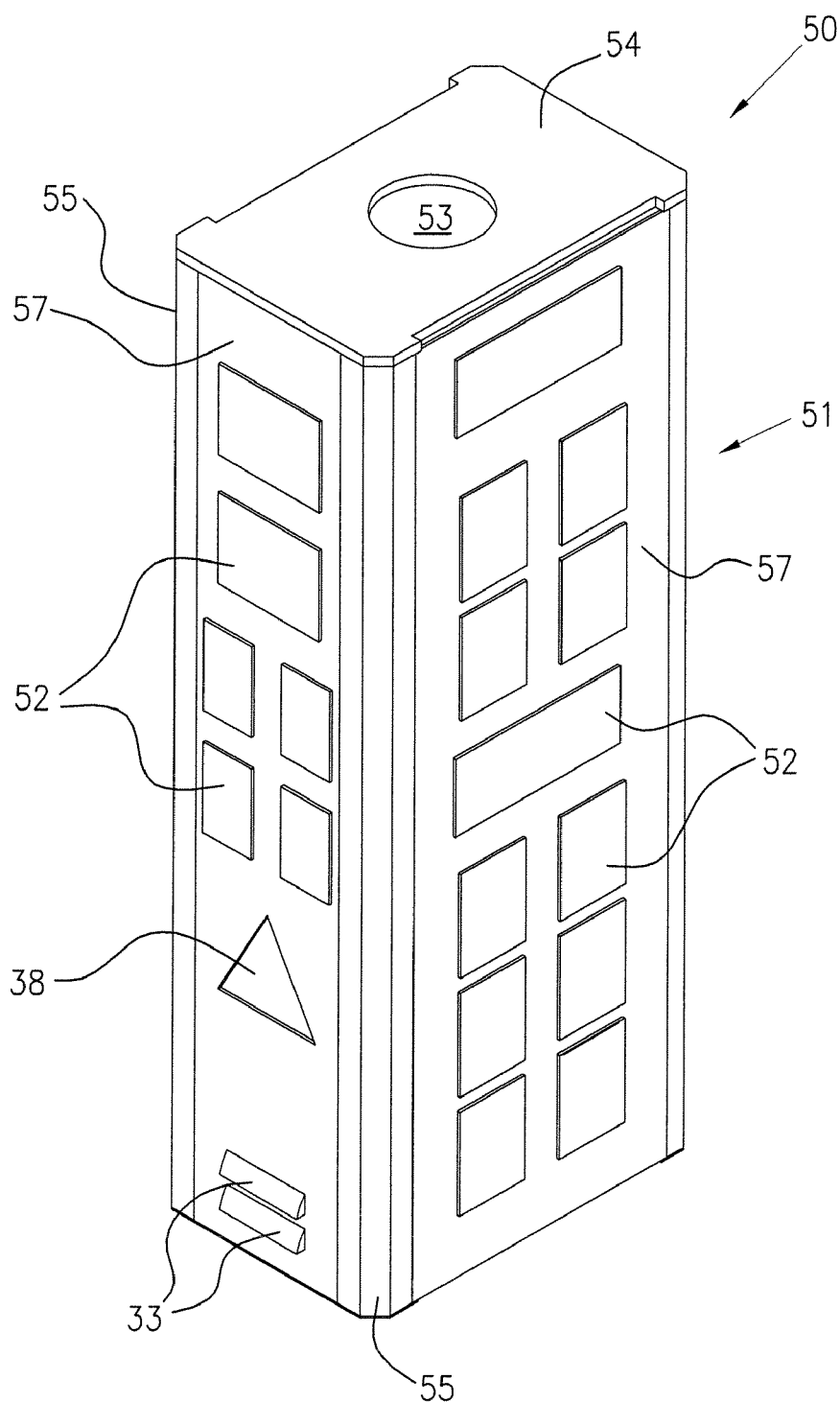
FIG. 15 is a perspective view of one embodiment of a surgical assembly control service head.

FIG. 15 is a perspective view depicting surgical assembly control service head 50 ("control service head 50"). A surgical assembly is herein defined as a surgical device, machine, or other equipment used in surgical procedures that requires power, such as electrical or pneumatic power to operate. Examples of surgical assemblies include, but are not limited to, ultrasonic surgical devices, electrocautery devices, insufflators, laser surgical instruments, cameras, light sources and endoscope devices. Also mounted on control service head 50 are devices that direct, control, and/or monitor a surgical vacuum and the flow of surgical gasses, such as oxygen, compressed air, nitrogen, and anesthetic gases. Service head housing 51 includes a plurality of walls 57 and is configured to contain one or more surgical assemblies, vacuum means 26 and filter socket 38. A filter similar in function to filter 10, described above, fits within filter socket 38. In the embodiment shown in FIG. 15, exhaust vents 33 are used in a similar manner to exhaust vents 33 described above. However, as explained below, other pathways may be used to direct the flow of filtered air.

Walls 57 of service head housing 51 contain knockout panels 52, which are provided to allow access to the surgical assemblies. Knockout panels 52 also allow cords, cables, power lines and other items to extend from the surgical assemblies to desired locations within the enclosure. Access is also provided for electrical outlets, such as US standard 120-volt outlets. In an alternate embodiment, service head housing 51 may include preformed holes, rather than knockout panels 52, to allow access to the surgical assemblies. It will be recognized that knockout panels may be placed in various locations on service head housing 51 to allow a custom arrangement of knockout panels 52.

An access hole 53 is shown defined by a top 54 of service head housing 51. Access hole 53 enables various control and power lines to extend into and out of service head housing 51 to reach surgical assemblies, vacuum means 26, and other components housed in or on service head housing 51. Access hole 53 may also provide a route for an exhaust duct through which vacuum means 26 forces air out of control service head 50.

Figure 16:
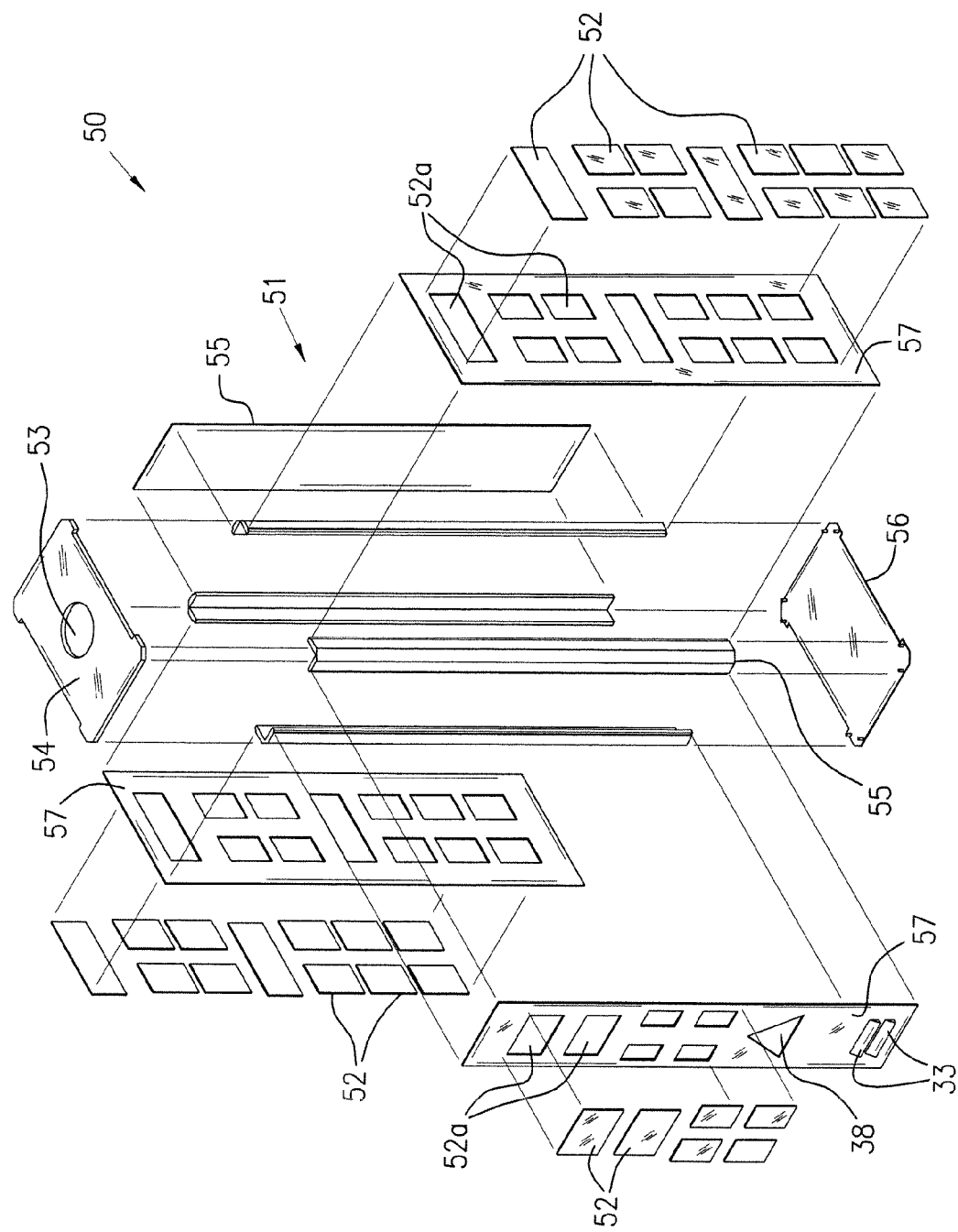
FIG. 16 is an exploded perspective view of one embodiment of a surgical assembly control service head.

FIG. 16 is an exploded perspective view of service head housing 51. In the embodiment shown, corners 55 are utilized to hold walls 57 and rear wall 55 into one integrated service head housing 51. It will be recognized that other means can be used to form service head housing 51 and that service head housing 51 may comprise more or less than four sides. Examples of alternate means to form service head housing 51 include, but are not limited to, a single sheet of metal formed into a multi-wall housing, screws, rivets, adhesives and other attaching devices known to those skilled in the art. Plastic materials may also be used to fabricate service head housing 51. In alternate embodiments, rear panel 55 may define one or more knockout panels 52 or accesses 52a similar to accesses 52a defined by panel walls 57. Bottom panel 56 may be used to form a completely enclosed service head housing 51.

Figure 17:
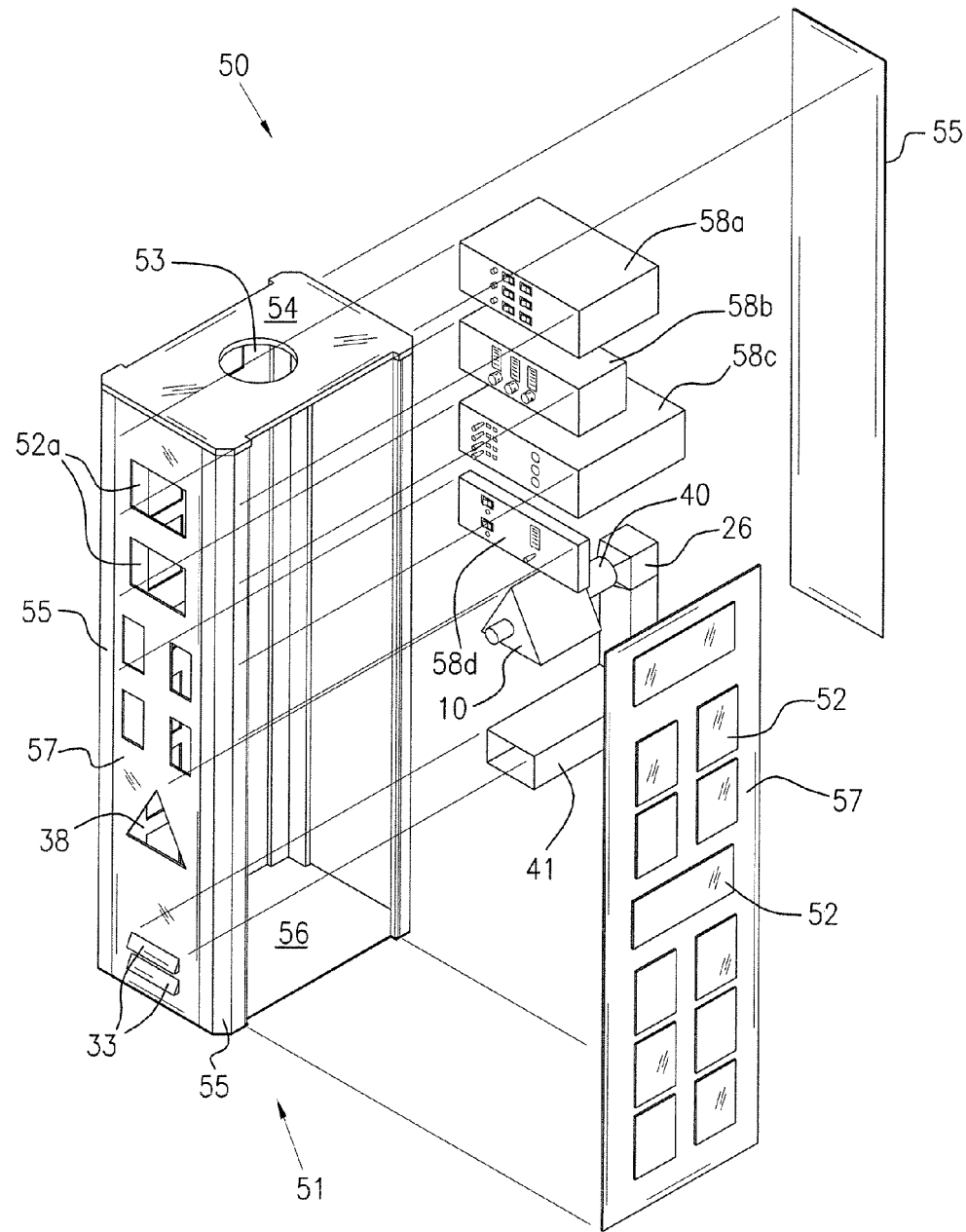
FIG. 17 is a partially exploded view of one embodiment of a surgical assembly control service head with a plurality of surgical assemblies and a filter.

FIG. 17 is a partially exploded perspective view of control service head 50. Filter 10 is shown connected to vacuum means 26, in this embodiment a vacuum motor. Filter 10 extends through access 38 to allow the intake of contaminated air from a fluid stream sourced within an enclosure, such as an operating room. Exhaust duct 41 is shown leading to exhaust vents 33 allowing the recirculation of filtered air to the enclosure. Surgical assemblies 58a-58d are shown being loaded into service head housing 51 through a back portion of service head housing 51. Rear panel 55 is then put in place to enclose the surgical assemblies 58. Shelves or parallel extensions extending from the side walls of service head housing 51 (not shown) or other equivalent structures may be used to hold surgical assemblies 58 within service head housing 51. In an alternate embodiment, some or all of surgical assemblies 58 or the controls for surgical assemblies may be on service head housing 51. Examples of surgical assemblies include, but are not limited to, laser surgery devices, insufflators, endoscope devices, cameras, light sources, and electrocautery devices. It is readily apparent that the controls for each surgical assembly 58 are easily accessed through accesses 52a enabling an operator, such as a surgeon, nurse, or technician, to easily control a particular surgical assembly 58 during an operation or other procedure. In addition, persons of ordinary skill in the art will recognize that service head housing 51 may be sized to hold any number and size or shape of surgical assemblies 58.

Figure 18:
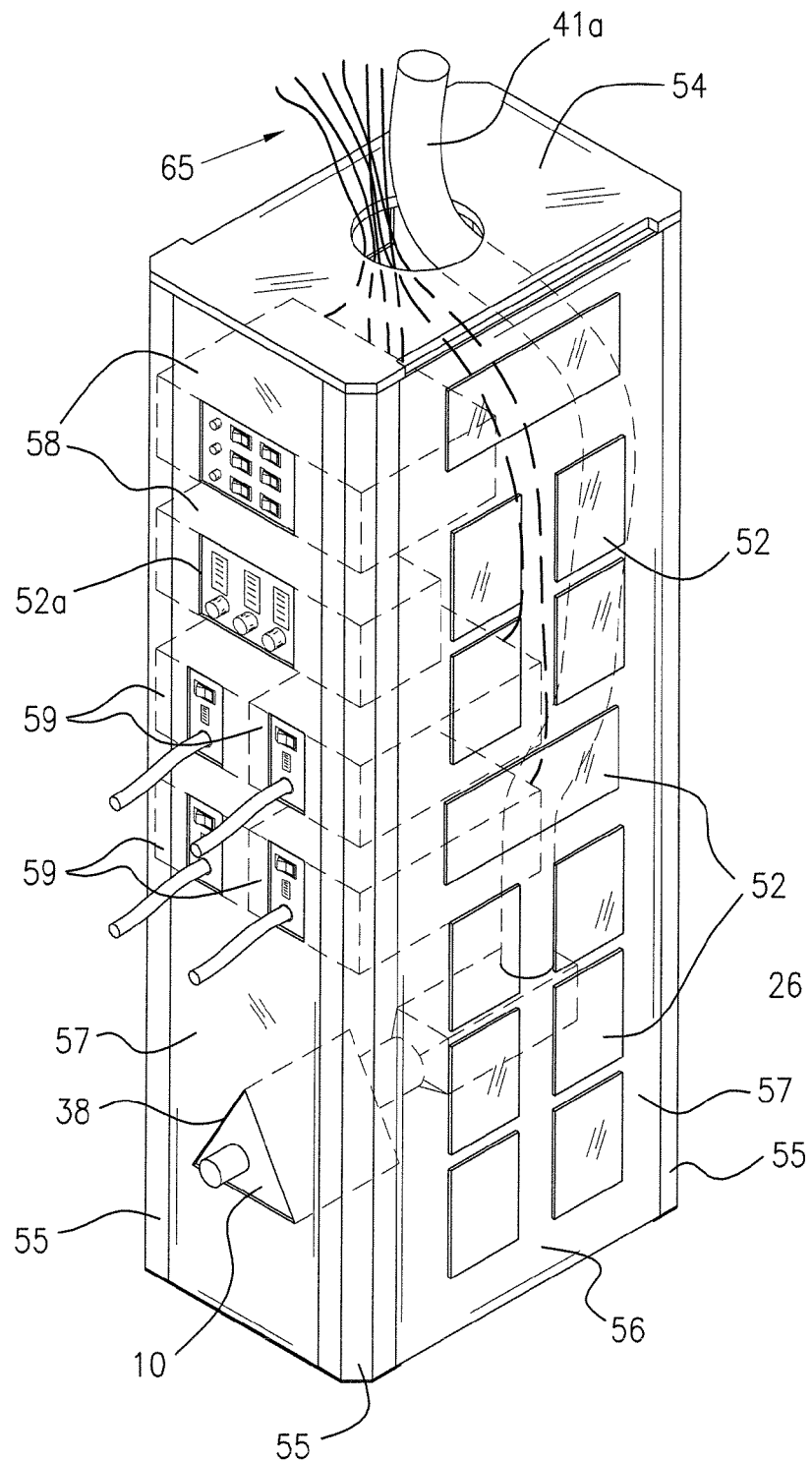
FIG. 18 is a perspective view of an alternate embodiment of a surgical assembly control service head having individual gas modules housed within the service head for receiving various gases.
Figure 19:
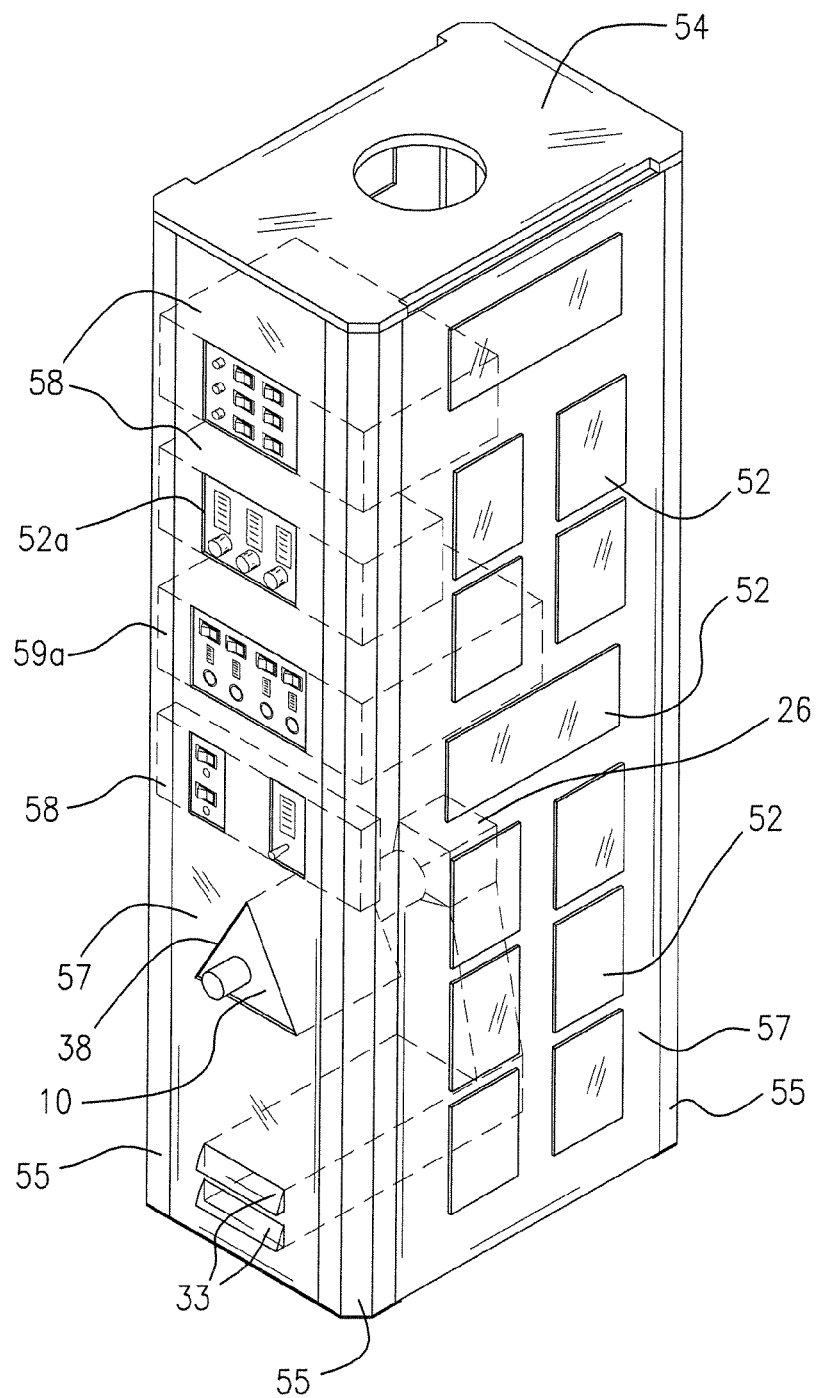
FIG. 19 is a perspective view of a second alternate embodiment of a surgical assembly control service head with a single gas control assembly.

FIG. 18 is a perspective view of service head housing 51 enclosing surgical assemblies 58. Also shown are gas control modules 59 for controlling the flow of surgical gases, such as oxygen, compressed air, and nitrogen, which may be used during a surgical procedure. FIG. 19 illustrates an alternate embodiment in which a single gas control module controls the output of multiple surgical gas inputs. FIG. 18 also depicts the arrangement of surgical assemblies 58 and gas control modules 59 in or on service head housing 51 along with a vacuum means for evacuating contaminants from a fluid stream originating from within an enclosure. As mentioned above, such contaminants may stem from a surgical procedure such as an electrocautery operation that creates smoke and/or particulate contaminants.

FIG. 18 also depicts an alternate embodiment in which the contaminant stream forced through filter 10 and vacuum means 26, is directed by vacuum means 26 through duct 41a out of service head housing 51 and out of the enclosure. As will be seen below, vacuum means 26 directs air through duct 41a into a building duct exhaust system, such as an HVAC, or into any interstitial space.

Figure 20:
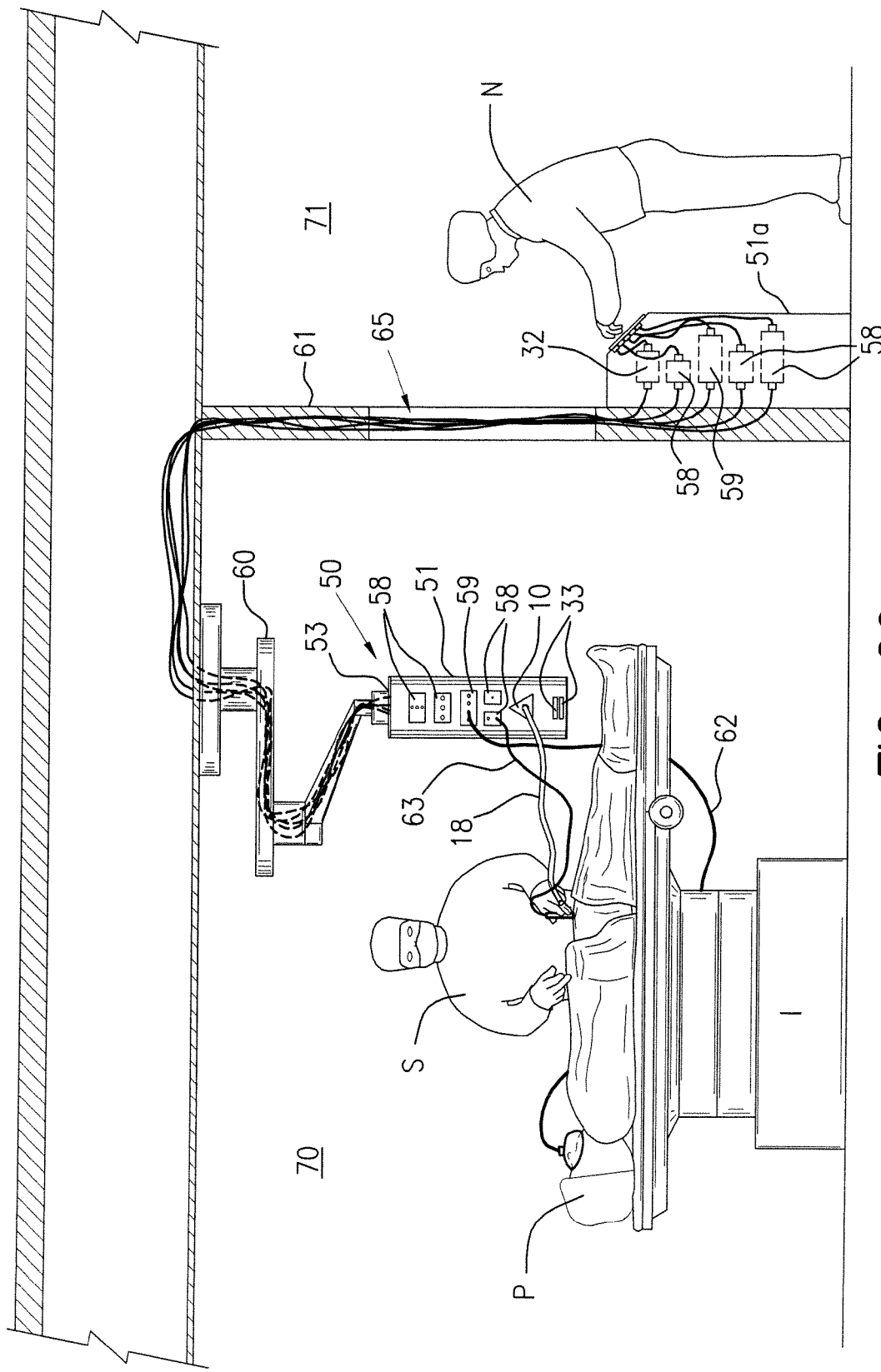
FIG. 20 depicts an embodiment of a surgical assembly control service head attached to an articulating arm mounted within an operating room wherein the surgical assembly control service head provides outlets for surgical assemblies that are controlled outside of the operating room.
Figure 21:
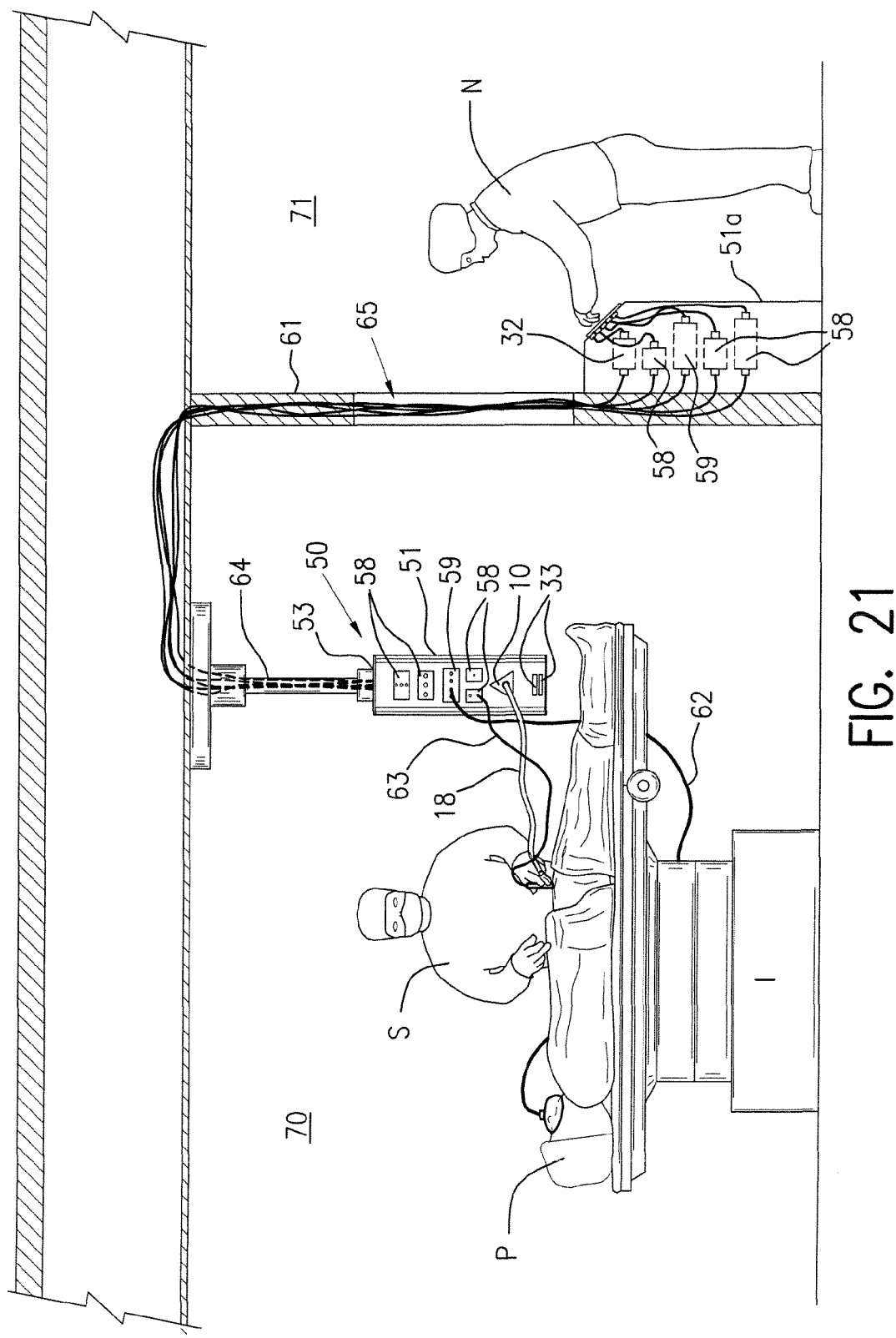
FIG. 21 depicts an embodiment of a surgical assembly control service head attached to a fixed arm mounted within an operating room wherein the surgical assembly control service head provides outlets for surgical assemblies that are controlled outside of the operating room.

FIG. 20 shows an embodiment of control service head 50 in a typical enclosure 70, such as an operating room, in which surgeon S is operating on patient P who is positioned on table T. In the embodiment shown, control service head 50 is mounted on an articulating arm 60 mounted in enclosure 70. Articulating arm 60 may be mounted in a convenient location that provides accessibility to control service head 50. As shown, surgical assemblies 58 are located outside of enclosure 70 in control room 71. Optionally, filter life timer 32 may be placed within control room 71, which may be separated from enclosure 70 by wall 61. Nurse or technician N operates each surgical assembly using communication devices including, but not limited to, intercoms, wireless communication systems, telephone or equivalent devices. Cords, power supplies, and other conductors (collectively conductors 65) extend from control panel 51a through articulating arm 60 through access hole 53 to surgical assemblies 58. In the embodiment shown, surgical assemblies 58 may be controlled by nurse N at control panel 51a with non-controlling outlets located in service head housing 51 that provide "plug-in" type outlets for conductors such as gas supply line 62 and electrocautery supply line 63. FIG. 21 shows an embodiment similar to that shown in FIG. 20 with control service head 50 attached to a fixed mounting 64. In this embodiment, control service head 50 is mounted in a fixed position. It will be recognized by those skilled in the art that conductors 65 may reach control service head 50 through articulating arm 60 or service head 64.

In an alternate embodiment, surgical assemblies 58 and/or other components are located in control area 71 or in other location(s) outside enclosure 70, while the switches, keypads, displays, knobs, and other devices that control and monitor those components may be located in control service head 50 within enclosure 70. Communication between the controls on control service head 50 and the various surgical assemblies 58 may be by microphones linked by cables or cords with USB connections, wireless communication arrays configured on 802.11 standards or equivalent systems, including systems using Bluetooth or other interfacing technology, fiber optic cables, hoses for gas or pneumatic operations and mechanical connections or combinations of these or equivalent components known in the art.

In addition, both control service head 50 and contaminant removal system 30 may be controlled using remote control devices such as an RS232 interface.

Figure 22:
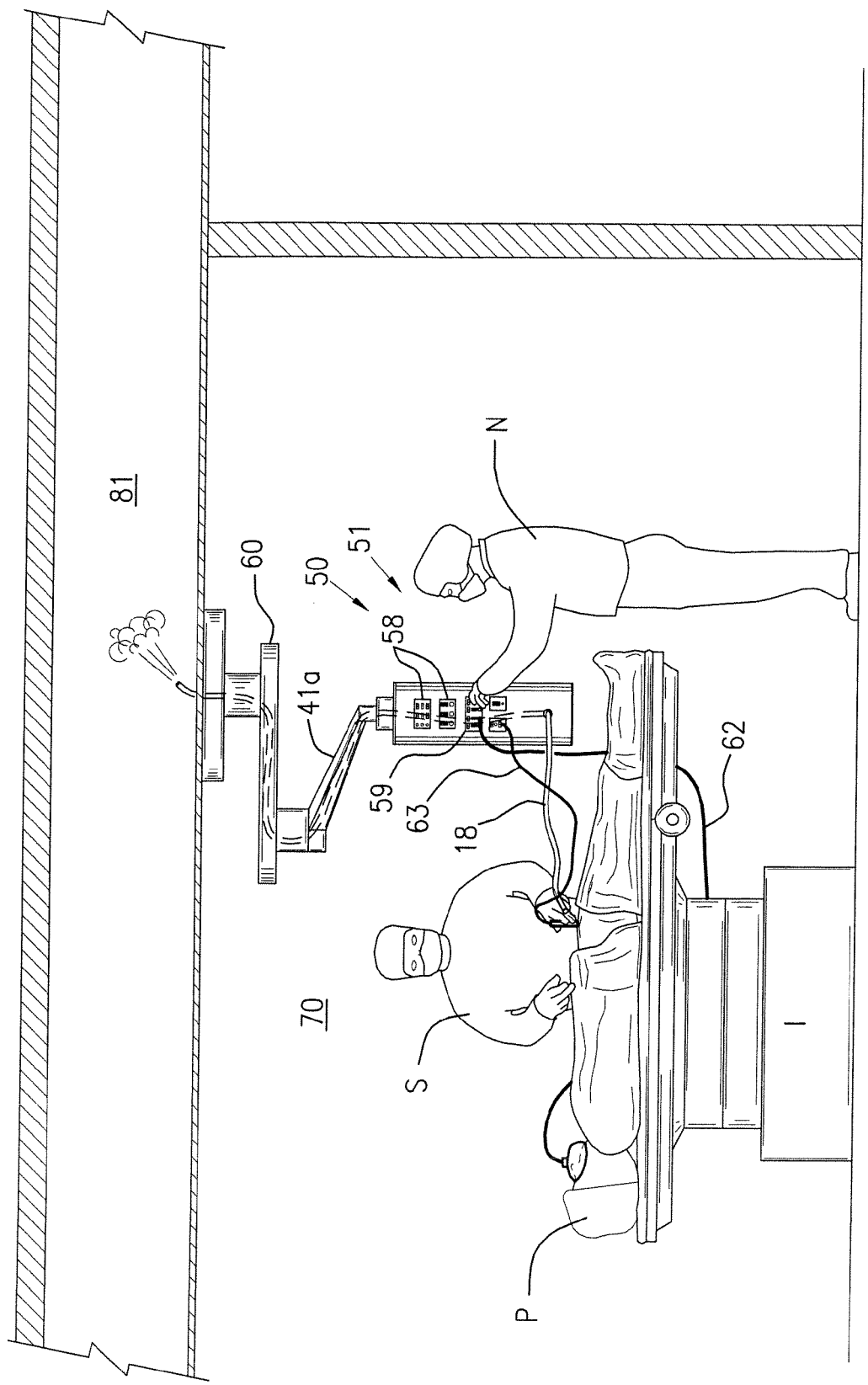
FIG. 22 depicts a surgical assembly control service head attached to an articulating arm mounted in an operating room in which surgical assemblies are mounted within the service head; and, FIG. 23 depicts a surgical assembly control service head mounted within an operating room, wherein surgical assemblies are mounted within the service head and a vacuum means is located outside the service head such that filtered air is exhausted into an HVAC duct.

FIG. 22 depicts an alternate embodiment in which surgical assemblies 58 and gas control modules 59 are housed in or on service head housing 51 located in enclosure 70. In this embodiment, access to the operational controls of surgical assemblies 58 and gas modules 59 is obtained through accesses 57a in service head housing 51. Toward that end, personnel in operating room 70, such as nurse N, operate surgical assemblies 58 and gas control modules 59 directly at control service head 50. In another alternate embodiment, control panel 32, which can display and control a filter life timer, may also be mounted in service head housing 51.

Figure 23:
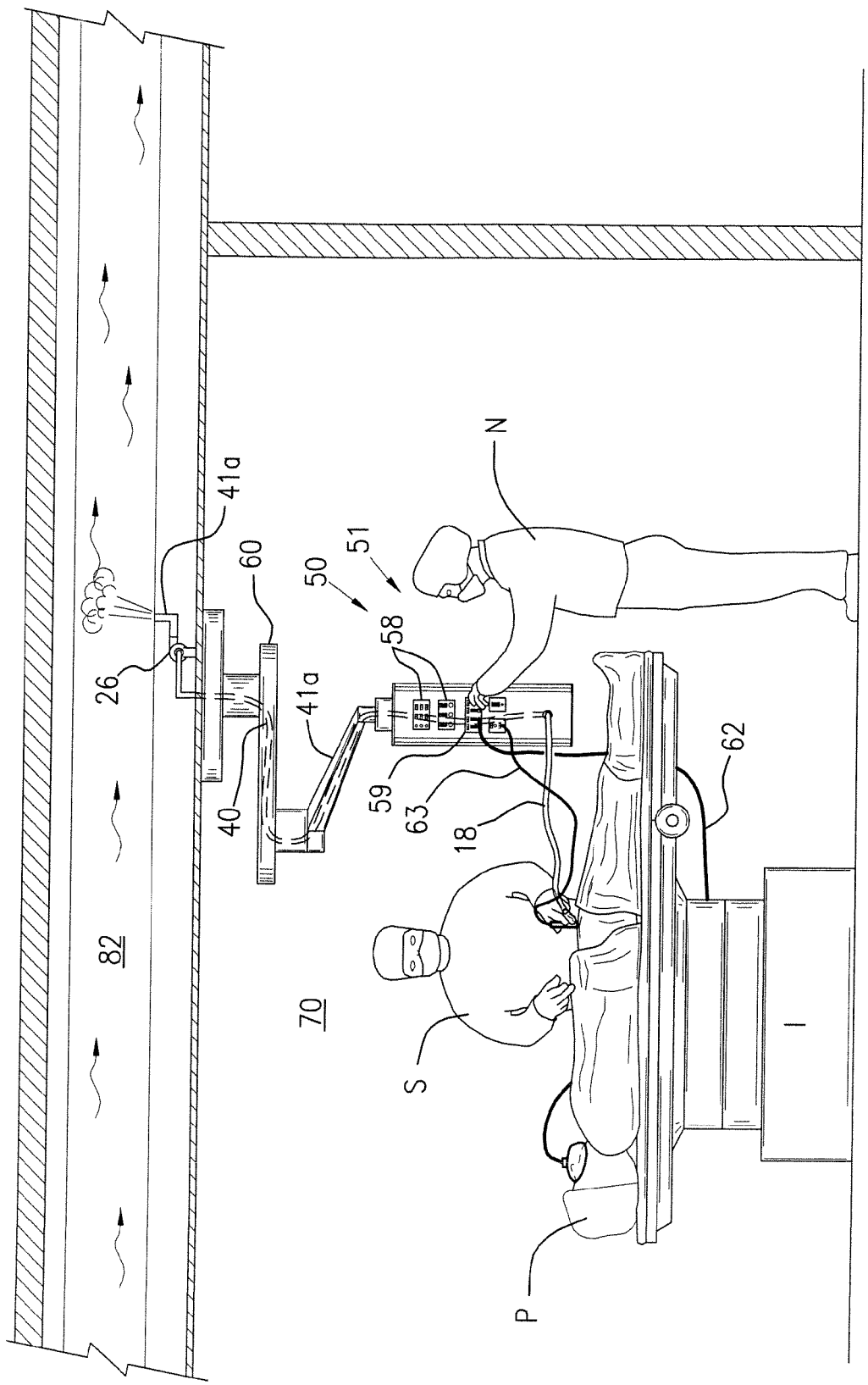

FIG. 22 also depicts one embodiment of the exhaust system of control service head 50. In FIG. 22, exhaust 41a is shown being discharged into interstitial space 81. Interstitial space 81 may be any space not within enclosure 70 or in a HVAC duct such as spaces between false ceilings and floor ceilings or the environment outside a building. In this embodiment, vacuum means 26, which may be located in service head housing 51, pulls the contaminant fluid stream through filter 10 and then pushes the filtered air out of housing 51 through access hole 53 and articulating arm 60 to the interstitial space. The filtered air may be pushed through one or more ducts 41a before being exhausted into an interstitial space. In an alternate embodiment, as shown in FIG. 23, vacuum means 26 may be located outside service head housing 51 and articulating arm 60. Similarly, filter 10 may be located in service head housing 51 or outside service head housing 51. In still another alternate embodiment, a plurality of filters may be used, each of which may be located in service head housing 51 or outside service head housing 51. FIG. 23 depicts the embodiment shown in FIG. 22 with the exhaust air being discharged into HVAC system 82. Again, in alternate embodiments, vacuum means 26 and filter 10 each may be located in or on service head housing 51 or separated from service head housing 51.

Thus it is seen that the objects of the invention are efficiently obtained, although changes and modifications to the invention should be readily apparent to those having ordinary skill in the art, which changes would not depart from the spirit and scope of the invention as claimed.

What is claimed is:

1. A filter device for surgical smoke evacuation, comprising:
   a housing adapted for mounting within a service head suspended off the floor;
   a cavity within said housing adapted to hold a filter media;
   a plurality of intake ports each said port configured to receive an intake tube for intake of smoke and other particulates originating from a surgical site;
   a plurality of intake port flaps wherein each said flap is configured for movement between a first position which substantially restricts passage of a gas or liquid through a corresponding port and a second position which allows passage of a gas or liquid through said corresponding port and filter media;
   wherein each said flap comprises a magnet;

wherein a portion of said housing comprises an attracting material configured to attract the magnet in at least one of said flaps and configured to hold said flap in said first position.

2. The filter device for surgical smoke evacuation of claim 1 wherein said attracting material is a magnet.

3. The filter device for surgical smoke evacuation of claim 1 wherein said attracting material is metal.

4. The filter device for surgical smoke evacuation of claim 1 wherein each said flap is comprised of a first portion and a second portion wherein said first and second portions are connected by a hinge.

5. The filter device for surgical smoke evacuation of claim 1 wherein each said flap further comprises a flexible material.

6. The filter device for surgical smoke evacuation of claim 1 wherein said housing comprises a surface adapted to receive an electrically-powered surgical assembly.

7. The filter device for surgical smoke evacuation of claim 1 further comprising a vacuum motor.

8. The filter device for surgical smoke evacuation of claim 1 further comprising a multi-layer filter media.

9. A multi-port filter system for surgical smoke evacuation, comprising:
- a housing adapted to hold a surgical filter;
- a first intake port configured to receive an intake tube of corresponding size, for intake of a fluid originating from a surgical site into said filter;
- a second intake port configured to receive an intake tube of corresponding size, for intake of a fluid originating from a surgical site into said filter, said second intake port having a larger diameter than said first intake port;
- intake port flaps corresponding to said first and second intake ports, wherein each said intake port flap is configured for movement between a first position which substantially restricts passage of a fluid through a corresponding intake port and a second position which allows passage of a fluid through said corresponding intake port;
- wherein each of said intake port flaps comprises a magnet; and
- wherein a portion of said housing comprises an attracting material configured to attract said magnets and hold said intake port flaps in said first position.

10. The multi-port filter system of claim 9, further comprising a third intake port configured to receive an intake tube of corresponding size, for intake of a fluid into said filter, said third intake port having a larger diameter than said second intake port.

11. The multi-port filter system of claim 9, further comprising an intake tube for intake of a fluid into said filter.

12. The multi-port filter system of claim 9 wherein each of said intake port flaps further comprises a flexible material.

13. The multi-port filter system of claim 9, further comprising a vacuum motor.

14. The multi-port filter system of claim 9, further comprising a multi-layer filter media.

* * * * *